US011713310B2

(12) United States Patent
Jain

(10) Patent No.: US 11,713,310 B2
(45) Date of Patent: Aug. 1, 2023

(54) CRYSTAL FORMS OF CRENOLANIB AND METHODS OF USE THEREOF

(71) Applicant: Arog Pharmaceuticals, Inc., Dallas, TX (US)

(72) Inventor: Vinay Jain, Dallas, TX (US)

(73) Assignee: Arog Pharmaceuticals, Inc., Dallas, TX (US)

(*) Notice: Subject to any disclaimer, the term of this patent is extended or adjusted under 35 U.S.C. 154(b) by 19 days.

(21) Appl. No.: 17/326,433

(22) Filed: May 21, 2021

(65) Prior Publication Data

US 2022/0017500 A1 Jan. 20, 2022

Related U.S. Application Data

(60) Provisional application No. 63/053,921, filed on Jul. 20, 2020.

(51) Int. Cl.
 *C07D 405/14* (2006.01)
(52) U.S. Cl.
 CPC ........ *C07D 405/14* (2013.01); *C07B 2200/13* (2013.01)
(58) Field of Classification Search
 CPC .................. C07D 405/14; C07B 2200/13
 See application file for complete search history.

(56) References Cited

U.S. PATENT DOCUMENTS

| | | | |
|---|---|---|---|
| 5,990,146 A | 11/1999 | Boschelli et al. | |
| 7,071,337 B2 | 7/2006 | Kath et al. | |
| 7,183,414 B2 | 2/2007 | Tom et al. | |
| 9,023,880 B2 | 5/2015 | Jain | |
| 9,101,624 B2 | 8/2015 | Jain | |
| 9,393,240 B2 | 7/2016 | Jain | |
| 9,480,683 B2 | 11/2016 | Jain | |
| 9,801,869 B2 | 10/2017 | Jain | |
| 9,801,870 B2 | 10/2017 | Jain | |
| 9,889,127 B2 | 2/2018 | Jain | |
| 10,213,423 B2 | 2/2019 | Jain | |
| 10,251,877 B2 | 4/2019 | Jain | |
| 10,780,086 B2 | 9/2020 | Jain | |
| 10,835,525 B2 | 11/2020 | Jain | |
| 2005/0124599 A1 | 6/2005 | Kath et al. | |
| 2007/0088032 A1 | 4/2007 | Tom et al. | |
| 2014/0194464 A1 | 7/2014 | Jain | |
| 2018/0117031 A1 | 5/2018 | Jain | |
| 2019/0183879 A1 | 6/2019 | Jain | |
| 2020/0188385 A1 | 6/2020 | Jain | |
| 2020/0375976 A1 | 12/2020 | Jain | |
| 2020/0390756 A1 | 12/2020 | Jain | |
| 2021/0052571 A1 | 2/2021 | Jain | |

FOREIGN PATENT DOCUMENTS

| | | | |
|---|---|---|---|
| EP | 2941251 A2 | 11/2015 | |
| WO | WO-1999016755 A1 | 4/1999 | |
| WO | WO-2001040217 A1 | 6/2001 | |
| WO | WO-2002032861 A2 | 4/2002 | |
| WO | WO-2002092599 A1 | 11/2002 | |
| WO | WO-2003024931 A1 | 3/2003 | |
| WO | WO-2003024969 A1 | 3/2003 | |
| WO | WO-2003035009 A2 | 5/2003 | |
| WO | WO-2003037347 A1 | 5/2003 | |
| WO | WO-2003057690 A1 | 7/2003 | |
| WO | WO-2003099771 A2 | 12/2003 | |
| WO | WO-2004005281 A1 | 1/2004 | |
| WO | WO-2004016597 A2 | 2/2004 | |
| WO | WO-2004018419 A2 | 3/2004 | |
| WO | WO-2004020431 A2 | 3/2004 | |
| WO | WO-2004039782 A1 | 5/2004 | |
| WO | WO-2004043389 A2 | 5/2004 | |
| WO | WO-2004046120 A2 | 6/2004 | |
| WO | WO-2004058749 A1 | 7/2004 | |
| WO | WO 2004/113322 | * 12/2004 | |
| WO | WO-2014107209 A2 | 7/2014 | |

OTHER PUBLICATIONS

Collins et al., "Results of a pilot study combining crenolanib with standard salvage chemotherapy in relapsed/refractory AML," EHA, Abstract EP639 (2020).
Daver et al., "Targeting FLT3 mutations in AML: review of current knowledge and evidence," Leukemia, 33: 299-312 (2019).
Fathi, "Emergence of crenolanib for FLT3-mutant AML," Blood, 122(22): 3547-3548 (2013).
Galanis et al., "Crenolanib is a Highly Potent, Selective, FLT3 TKI with Activity Against D835 Mutation," (Abstract Only) Blood, 120:1341 (2012).
Galanis et al., "Crenolanib is a potent inhibitor of FLT3 with activity against resistance-conferring point mutants" Blood, 123(1): 94-100 (2014).
Galanis et al., "Abstract 3660: Crenolanib: A next generation FLT3 inhibitor," Cancer Research, 72(8): Supplement, Abstract Only (2012).
Gao et al., "Combination of Crenolanib with Sorafenib Produces Synergistic Pro-Apoptotic Effects in FLT3-ITD-Inhibitor-Resistant Acute Myelogenous Leukemias with FLT3 Mutations" (Abstract Only), Blood, 120(21): 3591 (2012).
Goldberg et al., "Clinical benefit of crenolanib, with or without salvage chemotherapy, in multiply relapsed FLT3 mutant AML patients after prior treatment with gilteritinib," Blood, 136(Supp 1):8-9 (2020).

(Continued)

*Primary Examiner* — Valerie Rodriguez-Garcia
(74) *Attorney, Agent, or Firm* — Foley Hoag LLP; Dana M. Gordon; Laura Wzorek

(57) ABSTRACT

The present invention relates to novel crystalline polymorphs of 1-[2-[5-[(3-Methyl-3-oxetanyl)methoxy]-1H-benzimidazol-1-yl]-8-quinolinyl]-4-piperidinamine monobenzenesulfonate, and to methods for their preparation. The invention further relates to pharmaceutical compositions containing one or more forms and optionally one or more suitable pharmaceutical carriers. The invention also relates to methods of using the crystalline polymorphs of the invention in the treatment of disease.

16 Claims, 21 Drawing Sheets

(56) References Cited

OTHER PUBLICATIONS

Goldberg et al., "Younger patients with newly diagnosed FLT3-mutant AML treated with crenolanib plus chemotherapy achieve durable remissions," EHA 2020, Abstract EP451 (2020).
Hayashi et al., "Effects of Crenolanib, a Highly Selective Platelet-Derived Growth Factor Receptor ?/? (PDGFRA/B) Tyrosine Kinase Inhibitor, on the Proliferation of Kit-Mutant Gastrointestinal Stromal Tumor (GIST) Cells and Interstitial Cell of Cajal (ICC) Precursors," Gastroenterology, 142(5):S-30 (2012).
Heinrich et al., "Crenolanib inhibits the drug-resistant PDGFRA D842V mutation associated with imatinib-resistant gastrointestinal stromal tumors," Clinical Cancer Research, Clin Cancer Res, 18(16): 4375-4384 (2012).
Heinrich et al., "The effect of crenolanib (CP-868596) on phosphorylation of the imatinib-resistant D842V PDGFRA activating mutation associated with advanced gastrointestinal stromal tumors," Journal for Clinical Oncology, 29(15): Abstract No. 10012 (2011).
Heldin et al., "Involvement of platelet-derived growth factor ligands and receptors in tumorigenesis," J Intern Med, 283: 16-44 (2018).
Lewis et al., "Phase I Study of the Safety, Tolerability, and Pharmacokinetics of Oral CP-868,596, a Highly Specific Platelet-Derived Growth Factor Receptor Tyrosine Kinase Inhibitor in Patients With Advanced Cancers," J Clin Oncol, 27:5262-5269 (2009).
Michael et al., "Phase Ib sutdy of CP-868,596 a PDGFR inhibitor, combined with docetaxel with or without axitinib, a VEGFR inhibitor," British Journal of Cancer, 103: 1554-1561 (2010).
Oran et al., "Safety, tolerability and efficacy of crenolanib administered post allogeneic hematopoietic stem cell transplant (HSCT) in patients with FLT3 mutant AML" Blood, 136(Supp 1) (2020).
Randhawa et al., "Results of a Phase II Study of Crenolanib in Relapsed/Refractory Acute Myeloid Leukemia Patients (Pts) with Activating FLT3 Mutations," Blood, 124(21): 389-389 (2014).
Stone et al., "Clearance of phenotypically distinct FLT3-ITD and FLT3-TKD clones by treatment with crenolanib and chemotherapy as detected by longitudinal single-cell DNA sequencing analysis," EHA, Abstract EP584 (2020).
Tarlock et al., "Clinical benefit and tolerability of crenolanib in children with relapsed acute myeloid leukemia harboring treatment resistant FLT3 ITD and variant FLT3 TKD mutations treated on compassionate access," Blood, 136(Supp 1): 23-24 (2020).
Tsioumpekou et al., "Specific targeting of PDGFR? in the stroma inhibits growth and angiogenesis in tumors with high PDGF-BB expression," 10(3): 1122-1135 (2020).
Tyner et al., "Functional genomic landscape of acture mayloid luekaemia" Nature, 562: 526-531 (2018).
Wang et al., "Safety Study of Crenolanib, a Type I FLT3 Inhibitor, with Cytarabine/Daunorubicin or Cytarabine/Idarubicin Induction and High-Dose Cytarabine Consolidation in Newly Diagnosed FLT3+ AML," EHA Learning Center (2016).
Zhang et al., "Clinical resistance to crenolanib in acute myeloid leukemia due to diverse molecular mechanisms," Nature Communications, 10(1): 244 (2019).
International Search Report and Written Opinion for International Application No. PCT/US21/33618 dated Aug. 6, 2021.

* cited by examiner

US 11,713,310 B2

CRYSTAL FORMS OF CRENOLANIB AND METHODS OF USE THEREOF

RELATED APPLICATION

This application claims the benefit of priority to U.S. Provisional Patent Application Ser. No. 63/053,921, filed Jul. 20, 2020.

TECHNICAL FIELD OF THE INVENTION

The present invention relates to novel polymorphic forms of 1-[2-[5-[(3-Methyl-3-oxetanyl)methoxy]-1H-benzimidazol-1-yl]-8-quinolinyl]-4-piperidinamine, monobenzenesulfonate and to methods for their preparation and purification. The invention also relates to use of such forms in pharmaceutical compositions containing at least one polymorphic form, or compositions containing one substantially pure polymorphic form.

BACKGROUND OF THE INVENTION

Compound 1 (also referred to as "crenolanib besylate") is a potent and selective inhibitor of FMS-like tyrosine kinase 3 (FLT3) and platelet derived growth factor receptor (PDGFR) tyrosine kinases (Lewis, Lewis et al. 2009, Smith, Lasater et al. 2014). These kinases are mutated or aberrantly expressed in a number of proliferative diseases and pharmaceutical agents that target these kinases have had some success in treating such diseases. FLT3 is commonly mutated in acute myeloid leukemia, and drugs in development for treating this subgroup, including crenolanib besylate, have been successful in recent years (Wang 2019). PDGFR is mutated or aberrantly expressed in a large number of proliferative diseases included solid tumor cancers, and signalling through the PDGFR pathway plays an essential role in angiogenesis, the process by which new blood vessels are formed to provide nutrients to a growing tumor (Heldin, Lennartsson et al. 2017, Tsioumpekou, Cunha et al. 2020). Agents targeting angiogenesis cut off the blood supply and aid in inhibition of tumor growth.

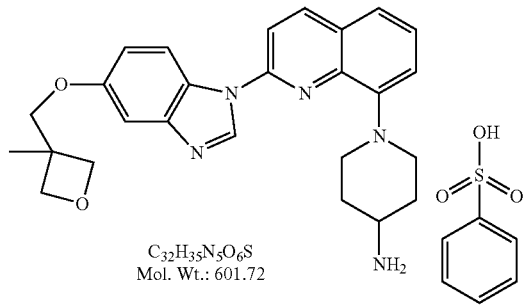

(Compound 1)

$C_{32}H_{35}N_5O_6S$
Mol. Wt.: 601.72

Compound 1 and pharmaceutically acceptable salts thereof are described in U.S. Pat. Nos. 7,019,147 and 7,071,337. The process and methods to manufacture Compound 1 are described in U.S. Pat. No. 7,183,414. The use of Compound 1 and pharmaceutically acceptable salts thereof in the treatment of proliferative disorders is described in U.S. Pat. Nos. 9,023,880 and 9,101,624.

SUMMARY OF THE INVENTION

The present invention is based on the discovery of several novel polymorphic forms of Compound 1. Each polymorphic form can be uniquely identified by several different analytical methods including, but not limited to, X-ray powder diffraction peaks, FT-IR spectra, or combinations thereof. The specific biochemical characteristics of the identified novel polymorphic forms are also detailed herein, especially as they pertain to the polymorph's stability, solubility, hygroscopicity, and other characteristics.

In some embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 7.1, 14.8, and 18.3. In another aspect, the crystalline form has additional peaks at diffraction angles (2Θ±0.2) 7.1, 14.8, 18.3, 24.3 and 26.9. In another aspect, the crystalline form has additional peaks at diffraction angles (2Θ±0.2) 7.1, 14.8, 16.0, 17.5, 18.2, 24.3, 25.3, and 26.9. In another aspect, the crystalline form has additional peaks at diffraction angles (2Θ±0.2) 7.1, 14.8, 16.0, 16.8, 17.5, 18.2, 19.7, 21.4, 24.3, 25.3, and 26.9. In another aspect, the crystalline form has additional peaks at diffraction angles (2Θ±0.2) 7.1, 8.0, 9.6, 11.4, 11.8, 13.9, 14.5, 14.8, 15.5, 16.0, 16.3, 16.8, 17.5, 18.2, 18.7, 19.3, 19.6, 19.7, 20.0, 20.3, 20.9, 21.4, 21.8, 22.6, 24.3, 25.3, 25.9, 26.9, 28.1, 29.5, 29.9, 31.0, 32.3, 33.4, and 34.3. In another aspect, the crystalline form is anhydrous. In a further aspect, the crystalline form has a melting point onset of 264° C. In another aspect, the crystalline form has a FT-IR spectrum comprising peaks at about 1479, 1271, 1185, 1033, 824, 751, 728, 690, 612, and 564 cm$^{-1}$. In another aspect, the crystalline form is non-hygroscopic. In another aspect, the crystalline form has a mass uptake of about 0.9% at 90% RH. In a further aspect, the crystalline form has birefringent, rod-like morphology by polarized light microscopy. In another aspect, the crystalline form is substantially pure.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 5.3, 18.7, and 23.0. In another aspect, the crystalline form powder x-ray diffraction pattern has additional peaks at diffraction angles (2Θ±0.2) 5.3, 12.8, 15.5, 18.7, and 23.0. In another aspect, the crystalline form powder x-ray diffraction pattern has additional peaks at diffraction angles (2Θ±0.2) 5.3, 12.8, 15.2, 15.5, 18.7, 23.0, and 24.2. In another aspect, the crystalline form powder x-ray diffraction pattern has additional peaks at diffraction angles (2Θ±0.2) 5.3, 12.8, 15.2, 15.5, 17.2, 18.7, 20.3, 23.0, 23.5 and 24.2. In another aspect, the crystalline form powder x-ray diffraction pattern has additional peaks at diffraction angles (2Θ±0.2) 3.3, 3.5, 3.8, 5.3, 6.1, 6.4, 8.0, 8.5, 8.8, 8.9, 9.6, 10.5, 11.1, 11.5, 12.4, 12.8, 13.1, 13.3, 13.7, 14.0, 14.2, 14.5, 15.9, 15.2, 15.5, 16.2, 17.0, 17.2, 17.6, 18.1, 18.7, 19.3, 19.8, 20.3, 20.9, 21.3, 22.0, 23.0, 23.5, 23.7, 24.2, 25.0, 25.6, 25.8, 26.4, 26.6, 27.4, 28.3, 28.6, 29.1, 29.4, 30.9, 31.5, 31.7, 31.9, 32.0, 32.2, 32.8, 33.8, 34.8, and 39.9. In another aspect, the crystalline form is a hemi-hydrate. In another aspect, the crystalline form has a melting point onset of about 174° C. In another aspect, the crystalline form has a FT-IR spectrum comprising peaks at about 1480, 1187, 1124, 1016, 821, 750, 728, 693, 613, and 563 cm$^{-1}$. In another aspect, the crystalline form is slightly hygroscopic. In another aspect, the crystalline form has a mass uptake of about 1.5% at 90% RH. In another aspect the crystalline form has highly birefringent rod-like morphology by polarized light microscopy. In another aspect the crystalline form is substantially pure.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 15.8, 19.8, and 21.7. In another aspect, the crystalline form powder x-ray diffraction pattern has additional peaks at diffraction angles (2Θ±0.2) 12.6, 15.8, 19.8, 20.5, and 21.7. In another aspect, the crystalline form powder x-ray diffraction pattern has additional peaks at diffraction angles (2Θ±0.2) 10.1, 12.6, 15.8, 19.8, 20.5, 21.7, 23.2, and 26.7. In another aspect, the crystalline form powder x-ray diffraction pattern has additional peaks at diffraction angles (2Θ±0.2) 7.4, 10.1, 12.6, 15.8, 18.5, 19.8, 20.5, 21.7, 22.8, 23.2, and 26.7. In another aspect, the crystalline form powder x-ray diffraction pattern has additional peaks at diffraction angles (2Θ±0.2) 2.1, 3.0, 6.3, 7.4, 7.9, 8.7, 10.1, 12.1, 12.6, 13.2, 13.4, 13.9, 14.9, 15.8, 16.3, 16.5, 16.7, 16.9, 17.3, 17.6, 18.5, 19.1, 19.3, 19.8, 20.5, 20.8, 20.9, 21.7, 22.0, 22.4, 22.8, 22.9, 23.2, 23.8, 24.3, 24.5, 25.1, 25.9, 26.1, 26.7, 27.0, 27.4, 27.6, 28.2, 28.9, 29.9, 30.1, 30.6, 31.0, 31.4, and 31.9. In another aspect, the crystalline form is anhydrous. In another aspect, the crystalline form has a melting point onset of about 251° C. In another aspect, the crystalline form has a FT-IR spectrum comprising peaks at about 1509, 1169, 1015, 954, 821, 799, 749, 728, 613, and 562 cm$^{-1}$. In another aspect, the crystalline form is slightly hygroscopic. In another aspect, the crystalline form has a mass uptake of about 1.5% at 90% RH. In another aspect, the crystalline form has highly birefringent rod-like morphology by polarized light microscopy. In another aspect, the crystalline form is substantially pure.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 4.8, 22.6, and 23.8. In another aspect, the crystalline form powder x-ray diffraction pattern has additional peaks at diffraction angles (2Θ±0.2) 4.8, 13.7, 20.6, 22.6, and 23.8. In another aspect, the crystalline form powder x-ray diffraction pattern has additional peaks at diffraction angles (2Θ±0.2) 4.8, 7.5, 13.7, 18.2, 20.6, 22.6, and 23.8. In another aspect, the crystalline form powder x-ray diffraction pattern has additional peaks at diffraction angles (2Θ±0.2) 4.8, 7.5, 13.7, 18.2, 18.4, 18.9, 20.0, 20.6, 22.6, and 23.8. In another aspect, the crystalline form powder x-ray diffraction pattern has additional peaks at diffraction angles (2Θ±0.2) 4.8, 6.3, 7.5, 9.3, 11.6, 13.4, 13.7, 14.5, 15.2, 15.4, 15.6, 16.7, 17.3, 17.8, 18.2, 18.4, 18.9, 19.4, 20.0, 20.2, 20.6, 20.9, 21.3, 22.6, 22.9, 23.8, 24.4, 24.8, 25.3, 26.2, 27.4, 27.8, 28.1, 28.3, 28.4, 28.9, 29.3, 29.8, 31.0, 32.1, 32.6, 33.3, and 34.2. In another aspect, the crystalline form is a solvate. In another aspect, the solvate form is a N,N'-dimethylacetamide solvate. In another aspect, the solvate form is an acetonitrile, butyl acetate, or ethanol solvate. In another aspect, the crystalline from has a degradation point onset of about 241° C. In another aspect, the crystalline form has a FT-IR spectrum comprising peaks at about 1479, 1272, 1184, 1033, 824, 751, 728, 690, 612, and 564 cm$^{-1}$. In another aspect the crystalline form is hygroscopic. In another aspect, the crystalline form has a mass uptake of 1.5% between 0% and 10% RH. In another aspect, the crystalline form has weakly birefringent with no defined morphology by polarized light microscopy. In another aspect, the crystalline form is substantially pure.

In other embodiments, the present invention includes a solid form of 1-[2-[5-[(3-Methyl-3-oxetanyl)methoxy]-1H-benzimidazol-1-yl]-8-quinolinyl]-4-piperidinamine monobenzenesulfonate wherein said form is amorphous.

In other embodiments, the present inventions includes a pharmaceutical composition comprising a crystalline form of 1-[2-[5-[(3-Methyl-3-oxetanyl)methoxy]-1H-benzimidazol-1-yl]-8-quinolinyl]-4-piperidinamine monobenzenesulfonate, its hydrates or solvates, and a pharmaceutically acceptable carrier.

In other embodiments, the present invention includes a method for the treatment of a subject suffering from a disease comprising administering a therapeutically effective amount of a crystalline form of Compound 1. In one aspect, the disease is a proliferative disorder. In one aspect, said proliferator disorder is selected from Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AMLITMDS), mixed lineage leukemia (MLL), myelodysplastic syndromes (MDS), myeloproliferative disorders (MPD), multiple myeloma, biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, uterine cancer, or other tumors.

In other embodiments, the present invention includes a process for the preparation of a crystalline form, comprising suspending 1-[2-[5-[(3-Methyl-3-oxetanyl)methoxy]-1H-benzimidazol-1-yl]-8-quinolinyl]-4-piperidinamine monobenzenesulfonate in 1,1-dimethoxymethane or 1-butanol; and then stirring or shaking until precipitation.

In other embodiments, the present invention includes a process for the preparation of a crystalline form, comprising suspending 1-[2-[5-[(3-Methyl-3-oxetanyl)methoxy]-1H-benzimidazol-1-yl]-8-quinolinyl]-4-piperidinamine monobenzenesulfonate in 98.5% ethanol/1.5% water (% v/v); and then shaking until precipitation.

In other embodiments, the present invention includes a process for the preparation of a crystalline form, comprising suspending 1-[2-[5-[(3-Methyl-3-oxetanyl)methoxy]-1H-benzimidazol-1-yl]-8-quinolinyl]-4-piperidinamine monobenzenesulfonate in 99% ethanol/1% toluene (% v/v); and then shaking until precipitation.

In other embodiments, the present invention includes a process for the preparation of a crystalline form, comprising suspending 1-[2-[5-[(3-Methyl-3-oxetanyl)methoxy]-1H-benzimidazol-1-yl]-8-quinolinyl]-4-piperidinamine monobenzenesulfonate in N,N'-dimethylacetamide, acetonitrile, butyl acetate, or ethanol; and then shaking until precipitation.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
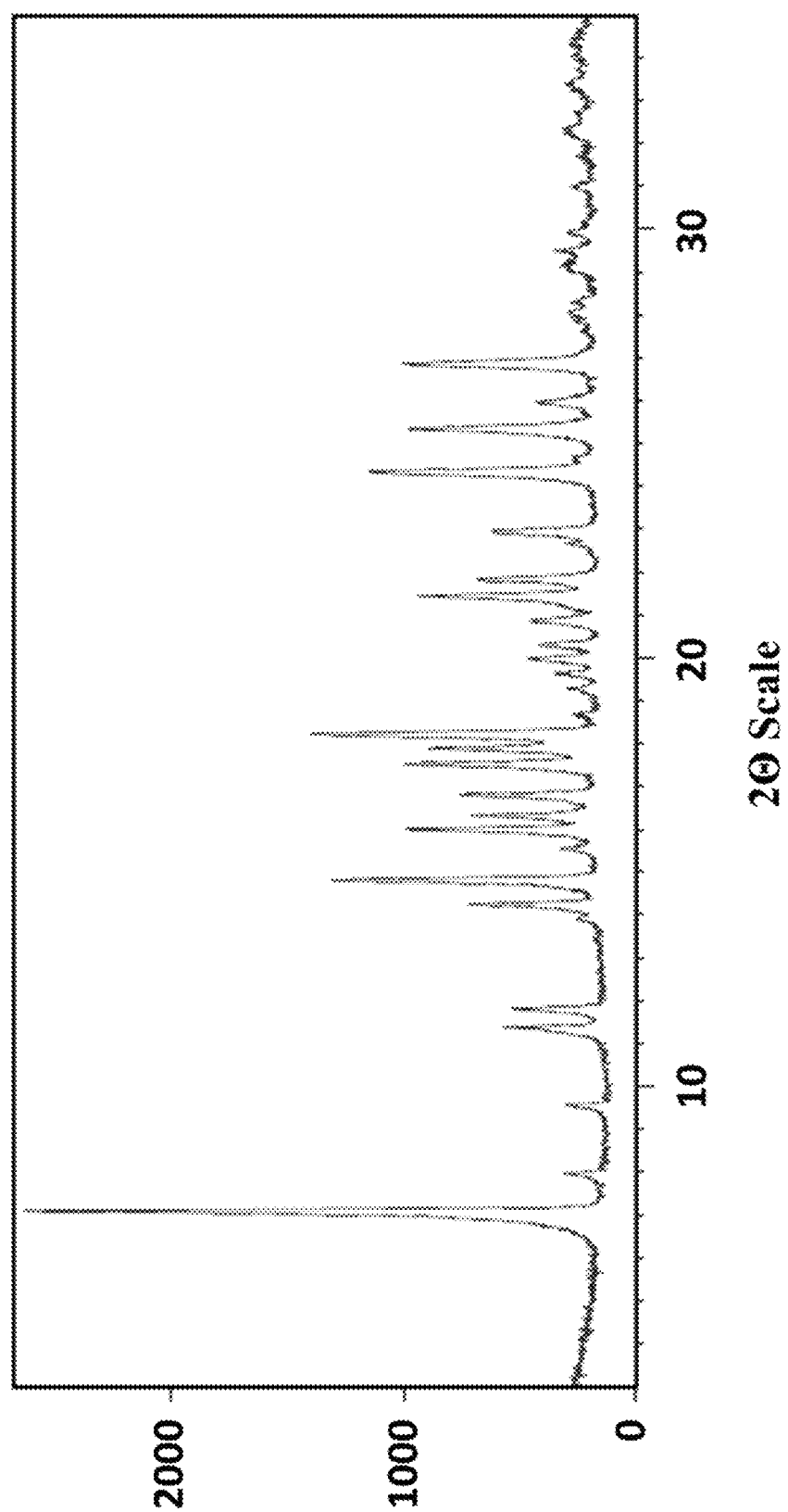
FIG. 1 presents the X-ray powder diffraction pattern of anhydrous Form I carried out on a PANalytical X'pert pro with PIXcel detector.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

Definitions

As used herein, the term "Compound 1" refers to the chemical compound crenolanib (1-(2-{5-[(3-methyl-3-oxetanyl)methoxy]-1H-benzimidazol-1-yl}-8-quinolinyl)-4-piperidinamine) or its benzene sulfonate salt. It is herein used interchangeably referred to as "Compound 1", "crenolanib", and "crenolanib besylate".

As used herein, the term "polymorph" or "polymorphic form" refers to different crystalline forms of the same compound. These forms include, but are not limited to, anhydrous forms, hydrates, hemi-hydrates, or solvates, and distinguished one from another by distinctive characteristics such as X-ray powder diffraction patterns.

As used herein, the term "substantially pure" in reference to a particular amorphous, crystalline, or polymorphic form means that the form includes less than 10% impurities by weight, preferably less than 5%, preferably less than 1% by weight of any other forms of the compound.

As used herein, the term "2 theta" or "2Θ" refers to the common measurement unit in diffraction patterns in which the angle between the incident beam and the reflected beam. The 2Θ values used in description of the novel polymorphic forms disclosed herein should be understood to refer to the experimental conditions used to characterise the forms. These experimental conditions are detailed herein.

The peak value at the diffraction angle θ, or at two times the diffraction angle θ (2θ), may exhibit a minor measurement error due to, e.g., instrumental error or variation in the conditions under which the measurement is taken. Accordingly, in certain embodiments, the characteristic peaks in the XRPD pattern have a value of $2\theta \pm 0.2°$. In certain embodiments, the characteristic peaks in the XRPD pattern have a value of $2\theta \pm 0.1°$. In certain embodiments, the characteristic peaks in the XRPD pattern have a value of $2\theta \pm 0.06°$.

As used herein, the term "amorphous" refers to a solid substance that lacks a defined three-dimensional structural order, or only has order over short distances, or both. Amorphous substances display XRPD patterns of a diffuse nature, with few or no sharp, defined peaks, instead displaying a small number of broad peaks.

As used herein, the term "crystalline" refers to a solid substance with a well-defined three-dimensional order. Crystalline substances display XPRD patterns with multiple sharp, defined peaks that are distinctive between different polymorphic forms.

As used herein, the term "anhydrous" refers to a solid substance that is crystalline and contains no water or solvent within the lattice structure.

As used herein, the term "hydrate" refers to a solid substance that is crystalline and incorporates water into the crystalline lattice structure in a stoichiometric or non-stoichiometric amount.

As used herein, the term "hemi-hydrate" refers to a solid substance that is crystalline and incorporates one molecule of water for every two molecules of compound 1 within the lattice structure.

As used herein, the term "solvate" refers to a solid substance that is crystalline and incorporates solvent molecules within the lattice structure. In certain embodiments, there is one molecule of solvent for every one molecule of compound 1 within the lattice structure. In certain embodiments, there are two molecules of solvent for every two molecules of compound 1 within the lattice structure As used herein, the term "XRPD pattern" refers the diffraction pattern observed when a form of compound 1 is subjected X-ray powder diffraction under the experimental conditions that are defined herein.

As used herein, the term "FT-IR" or "Fourier-transformed infrared spectroscopy" refers to the infrared spectrum observed from a given form of compound 1 under the experimental conditions defined herein.

As used herein, the term "birefringent" refers to phenomenon in which a material's refractive index is dependent on the polarization of light, which results in a contrast image when viewed through a microscope with polarizing filters, as detailed herein.

As used herein, the term "hygroscopicity" refers to the capacity of a form of compound 1 to absorb or release water vapor when exposed to humidity. Hygroscopic forms absorb water in normal or humid conditions, which affects the physical characteristics and can make a specific form unsuitable for pharmaceutical compositions and long-term stability.

As used herein, the term "DSC" refers to differential scanning calorimetry which is used to determine phase transitions (e.g. melting point) and other events such as loss of solvent or water molecules and recrystallization of a form. The experimental conditions used to characterize the novel polymorphic forms disclosed are detailed herein.

As used herein, the term "TGA/DSC" refers to simultaneous thermogravimetric analysis and differential scanning calorimetry used to determine the hydrated/solvated status of a novel polymorphic form. The experiment conditions used to characterize the novel polymorphic forms disclosed are detailed herein.

As used herein, the term "disease" refers to a disorder in a subject, including a human subject, that produces specific signs or symptoms.

As used herein, the terms "proliferative disease" or "proliferative disorder" refer to excess cell proliferation of one or more subset of cells in a multicellular organized resulting in harm (i.e. discomfort or decreased life expectancy) to the multicellular organism. Proliferative disorders can occur in different types of animals and humans. As used herein, these terms include neoplastic disorders or cancers. Non-limiting examples of proliferative disorders for treatment with the present invention include leukemia, myeloma, myeloproliferative disease, myelodysplastic syndrome, idiopathic hyperesosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

As used herein, the term "composition" refers to a product comprising the specified ingredients in the specified amounts, as well as any product which results, directly or indirectly, from combinations of the specified ingredients in the specified amounts. In one example, the composition includes crenolanib or a pharmaceutically acceptable salt thereof (e.g. the benzene sulfonate salt) in an amount sufficient for the treatment of a disease.

Pharmaceutical compositions for use may contain one or more pharmaceutically acceptable carriers including excipients or auxiliaries such as stabilizers, diluents, dispersing agents, suspending agents, and/or thickening agents which facilitate the processing of preparations acceptable for use in the treatment of disease in a mammal. The choice of administration route will inform the proper formulation using techniques, carriers, and explements known in the art. Suitable pharmaceutical carriers include inert diluents or fillers, water and various organic solvents. The pharmaceutical compositions may, if desired, contain additional ingredients such as flavorings, binders, excipients and the like. Thus, for oral administration, tablets containing various excipients such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and β-hydroxypropyl-β-cyclodextrins, or other solubilized derivatives may also be advantageously used to enhance delivery of compounds of the formulae described herein.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as DiPac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The term "therapeutically effective amount" as used herein, refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Compounds of the present invention may be administered to a subject systemically, for example, orally, intravenously, subcutaneously, intramuscularly, intradermally, or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders; or liquid forms, such as solutions, emulsions, and suspensions. Forms useful for parenteral administration include sterile solutions, emulsions and suspensions. Forms useful for topical administration include ointments or creams. Forms useful for rectal administration include suppositories. In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

The daily dosage of the compounds of the present invention may be varied over a wide range from 50 to 500 mg per adult human per day. For oral administration, the compositions are preferably provided in the form of tablets containing 20, 60, 80, or 100 milligrams. The compounds of the present invention may be administered on a regimen up to three times or more per day, preferably three times per day. Optimal doses to be administered may be determined by those skilled in the art, and will vary with the polymorphic form of the present invention used, the mode of administration, the time of administration, the strength of the preparation, the details of the disease condition. Factors associated with patient characteristics, such as age, weight, and diet will call for dosage adjustments.

General synthetic methods which may be referred to for preparing Compound 1 are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application No. US 2005/0124599 (Pfizer, Inc.) and U.S. Pat. No. 7,183,414 (Pfizer, Inc.), relevant portions incorporated herein by reference.

Experimental Conditions Used to Characterize Novel Polymorphic Forms

Each identified novel polymorphic crystalline form was characterized using conventional methods used in the art. The detailed methods of the experimental conditions used for such characterization are detailed herein.

The X-ray powder diffraction (XRPD) patterns of the identified polymorphic forms were carried out on a PANAlystical X'pert Pro with PIXcel detector (128 channels), scanning the samples between 3 and 35° 2Θ. The material was gently ground to release any agglomerates and loaded onto a multi-well plate with Kapton or Mylar polymer film to support the sample. The multi-well plate was then place into the diffractometer and analyzed using CuK radiation ($\alpha_1\lambda$=1.5460 Å; $\alpha_2$=1.54443 Å; $\beta$=1.39225 Å; $\alpha_1$: $\alpha_2$ ratio=0.5) running in transmission mode (step size 0.0130° 2Θ, stem time 18.87 s) using 40 kV/40 mA generator settings. Data were visualized and images generated using the HighScore Plus 4.7 desktop application (PANalytical, 2017). The peak values for each form are summarized in tables below, along with the relative intensity of each identified peak.

It will be appreciated by those skilled in the art that peak positions (2Θ) and peak intensity will show some variability between different apparatus and experimentation conditions, typically by ±0.2 degrees. Accordingly, where peak positions are reported herein, one with skill in the art will appreciate that such numbers are intended to encompass this variability. Further, those skilled in the art will appreciate that the relative peak intensities, as displayed in both diffractogram patterns and the peak tables disclosed herein, will also vary between apparatus as well as other external factors such as degree of crystallinity, preferred orientation, and others.

Thermogravimetric Analysis/Differential Scanning Calorimetry (TGA/DSC) was used to determine the phase transition and degradation points as well as the hydrated/solvated states of the various polymorphic forms identified. Approximately 5-10 milligrams of material was added into a pre-tared open aluminum pan and loaded into a TA Instruments SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 cm$^3$/min. Skilled artisans will appreciate that ambient laboratory conditions may cause slight variability in these readings.

Differential Scanning Calorimetry was used to determine the melting point of stable polymorphic forms. Approximately 1-5 milligrams of material was weighed into an aluminum DSC pan and sealed non-hermetically with an aluminum lid. The sample pan was then loaded into a TA Instruments Discovery DSC 2500 differential scanning calorimeter equipped with a RC90 cooler. The sample and reference were heated to 240° C. at a scan rate of 10° C./min and the resulting heat flow response monitored. The sample was re-cooled to 20° C. and then reheated again to 325° C. all at 10° C./min. Nitrogen was used as the purge gas, at a flow rate of 50 cm$^3$/min. Skilled artisans will appreciate that ambient laboratory conditions may cause slight variability in these readings.

Fourier Transformed Infrared Spectroscopy was performed on the stable polymorphic forms identified to further characterize these forms. These experiments were carried out on a Bruker ALPHA P spectrometer. Sufficient material was placed onto the center of the plate of the spectrometer and the spectra were obtained using a resolution of 4 cm$^{-1}$, background scan time of 16 scans, sample scan time of 16 scans, data collection of 4000 to 400 cm$^{-1}$, and result spectrum were generated on the basis of transmittance. Spectra were analyzed and generated using OPUS version 6 computer software.

Dynamic Vapor Sorption (DVS) was used to determine the hygroscopicity of stable polymorphic forms. Approximately 10-20 milligrams of sample was placed in to a mesh vapor sorption balance pan and loaded into an intrinsic dynamic vapor sorption balance by Surface Measurement Systems. The sample was subjected to ramping profile from 40-90% relative humidity (RH) at 10% increments, maintain the sample at each step until as table weight had been achieved (dm/dt 0.0004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample tot be determined. XRPD was then carried out on any solid retained to determine if there was change between polymorphic forms during the process.

The presence of crystallinity (birefringence) was determine using polarized light microscopy. Samples were imaged using an Olympus BX50 microscope equipped with cross-polarizing lenses and a Motic camera. Images were captured using Motic Images Plus 2.0. All images were recorded using the 20× objective.

Novel Polymorphic Forms of Compound 1

Polymorphic Form I

Polymorphic Form I of Compound 1 is an anhydrous crystalline form of the besylate salt. Methods for producing Compound 1 are detailed in U.S. Pat. No. 7,183,414. Polymorphic Form I was produced by slurrying the amorphous form of the besylate salt of Compound 1 in 1,1-dimethoxymethane or 1-butanol, by adding approximately 5 volumes of solvent to 10 mg of amorphous Compound 1, with shaking under ambient conditions. The slurry was then matured using thermal cycling, using 4-hour cycles of ambient and 40° C. temperatures for approximately 24 hours, after which the solids were isolated via centrifugation and dried for 24 hours in a 40° C. oven. XRPD analysis after initial solubility screening, of the wet solid post-thermal cycling maturation, and of the dried solid confirmed that only Polymorph Form I was present.

Form I has several unexpected advantages over the amorphous form and other polymorphic forms identified herein. As an anhydrous form, Form I is not subject to the potential impurities that may be associated with solvated or hydrated form. In addition, though Form III is the most thermodynamically stable crystalline form under competitive slurry conditions (i.e., Form I will convert to Form III when Form III seeds are present in a slurry), Form I has a higher temperature for onset of degradation and is non-hygroscopic with a mass uptake of 0.9% at 90% RH, making this form more suitable for long-term storage under variable conditions and for processing for pharmaceutical compositions and forms such as tablets. Form I has increased flowability and tabletability. Form I also has mixing properties suitable for dry granulation with both low and high dose formulations. This limits the need for solvents during production of the pharmaceutical product, limiting the possibility of contamination from solvents and maintaining high ratios of active drug to excipient levels. In addition, as Form I does not convert to Form III in the absence of seeding, has a higher temperature of degradation onset, and is stable at ambient conditions for long-term storage, Form I is ideally suited for standard pharmaceutical compositions in various forms such as tablets or capsules.

Crystalline Form I was characterized by the XRPD pattern shown in FIG. 1. Table 1 shows the position of the peaks (expressed as 2Θ) and relative intensity, of the XPRD pattern for Form I as measured on a PANAlytical X'pert Pro with CuK radiation as detailed herein.

TABLE 1

| Angle (Degree 2Θ) | Relative Intensity (%) |
| --- | --- |
| 7.1 | 100.0 |
| 8.0 | 6.8 |
| 9.6 | 7.6 |
| 11.4 | 16.5 |
| 11.8 | 16.0 |
| 13.9 | 2.2 |
| 14.5 | 22.6 |
| 14.8 | 45.2 |
| 15.5 | 4.9 |

TABLE 1-continued

| Angle (Degree 2Θ) | Relative Intensity (%) |
| --- | --- |
| 16.0 | 32.4 |
| 16.3 | 19.3 |
| 16.8 | 22.8 |
| 17.5 | 30.5 |
| 17.9 | 28.8 |
| 18.2 | 49.6 |
| 18.7 | 2.8 |
| 19.3 | 4.6 |
| 19.6 | 6.2 |
| 20.0 | 11.1 |
| 20.3 | 8.8 |
| 20.9 | 10.4 |
| 21.4 | 26.8 |
| 21.8 | 20.6 |
| 22.6 | 4.1 |
| 22.9 | 17.9 |
| 24.3 | 37.7 |
| 25.3 | 32.2 |
| 25.9 | 9.2 |
| 26.9 | 33.9 |
| 28.1 | 2.5 |
| 29.5 | 5.5 |
| 29.9 | 4.1 |
| 29.9 | 3.7 |
| 31.0 | 2.9 |
| 32.3 | 3.6 |
| 33.4 | 2.9 |
| 34.3 | 1.9 |

Figure 2:
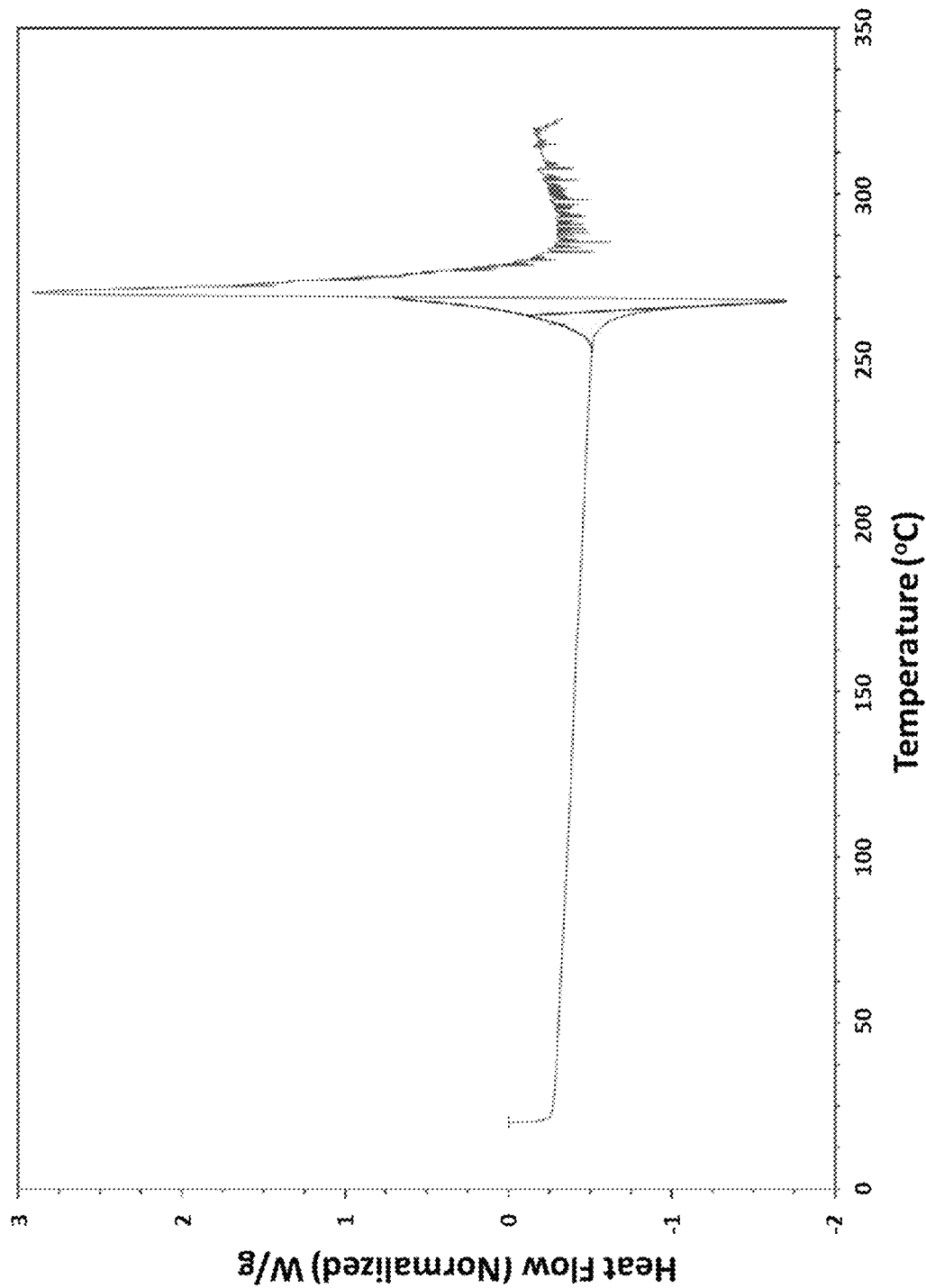
FIG. 2 presents a DSC thermogram of anhydrous Form I carried out on a TA Instruments Discover DSC 250 differential scanning calorimeter equipped with a RC90 cooler using a heating rate of 10° C./min.

Crystalline Form I was also characterized by DSC (FIG. 2). TGA/DSC showed a small endothermic event with onset at 264° C. and peak at 268° C. immediately followed by a sharp exothermic event, associated with a melt and degradation event. Melt and degradation was associated with a 2.5% mass loss as measured by TGA.

Figure 3:
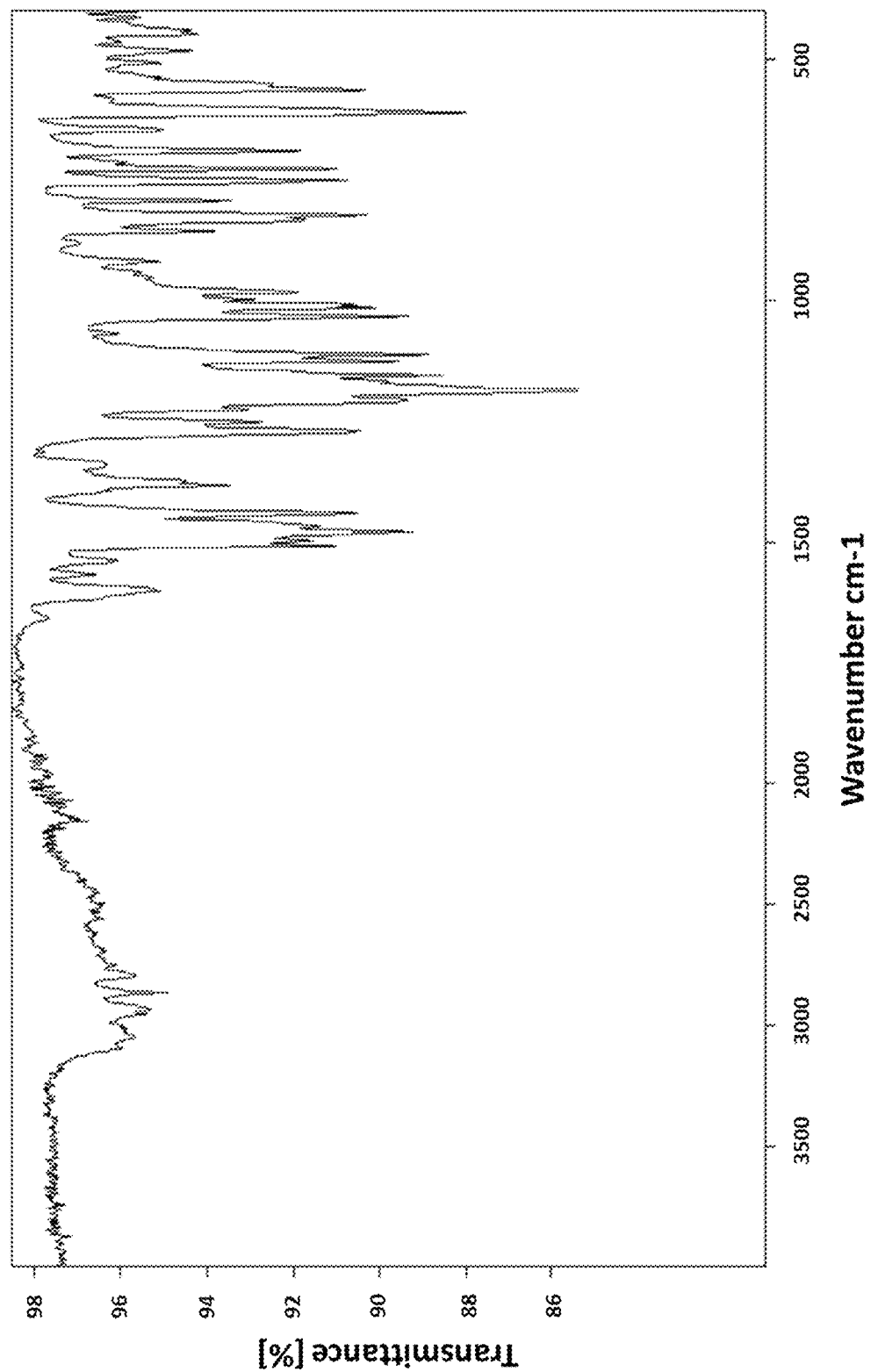
FIG. 3 presents the Fourier Transformed Infrared Spectroscopy spectrum of anhydrous Form I carried out on a Bruker ALPHA P spectrometer.

Infrared spectrometry (FT-IR) was used to further characterize Form I of Compound 1. FIG. 3 shows the FT-IR spectra of Form I. The complete list of peak positions presented as wavenumber ($cm^{-1}$) and their relative intensity is included in Table 2.

TABLE 2

| Wavenumber ($cm^{-1}$) | Relative Intensity |
| --- | --- |
| 3098 | 0.003 |
| 3048 | 0.009 |
| 2954 | 0.003 |
| 2935 | 0.012 |
| 2864 | 0.031 |
| 2796 | 0.01 |
| 2751 | 0.003 |
| 2626 | 0.002 |
| 2558 | 0.006 |
| 2497 | 0.004 |
| 2452 | 0.003 |
| 2402 | 0.002 |
| 2158 | 0.012 |
| 1600 | 0.026 |
| 1568 | 0.011 |
| 1540 | 0.013 |
| 1502 | 0.017 |
| 1497 | 0.009 |
| 1479 | 0.09 |
| 1467 | 0.012 |
| 1440 | 0.047 |
| 1383 | 0.044 |
| 1373 | 0.004 |
| 1337 | 0.011 |
| 1271 | 0.066 |
| 1251 | 0.023 |
| 1226 | 0.015 |
| 1206 | 0.018 |
| 1185 | 0.13 |

TABLE 2-continued

| Wavenumber (cm⁻¹) | Relative Intensity |
| --- | --- |
| 1154 | 0.025 |
| 1125 | 0.032 |
| 1113 | 0.054 |
| 1068 | 0.006 |
| 1033 | 0.076 |
| 1017 | 0.037 |
| 1009 | 0.006 |
| 998 | 0.031 |
| 984 | 0.025 |
| 941 | 0.004 |
| 920 | 0.016 |
| 882 | 0.005 |
| 858 | 0.025 |
| 833 | 0.008 |
| 824 | 0.073 |
| 794 | 0.037 |
| 751 | 0.071 |
| 728 | 0.064 |
| 713 | 0.006 |
| 690 | 0.056 |
| 647 | 0.028 |
| 612 | 0.099 |
| 564 | 0.063 |
| 509 | 0.013 |
| 484 | 0.022 |
| 464 | 0.005 |
| 449 | 0.024 |
| 440 | 0.005 |
| 414 | 0.011 |

Figure 4:
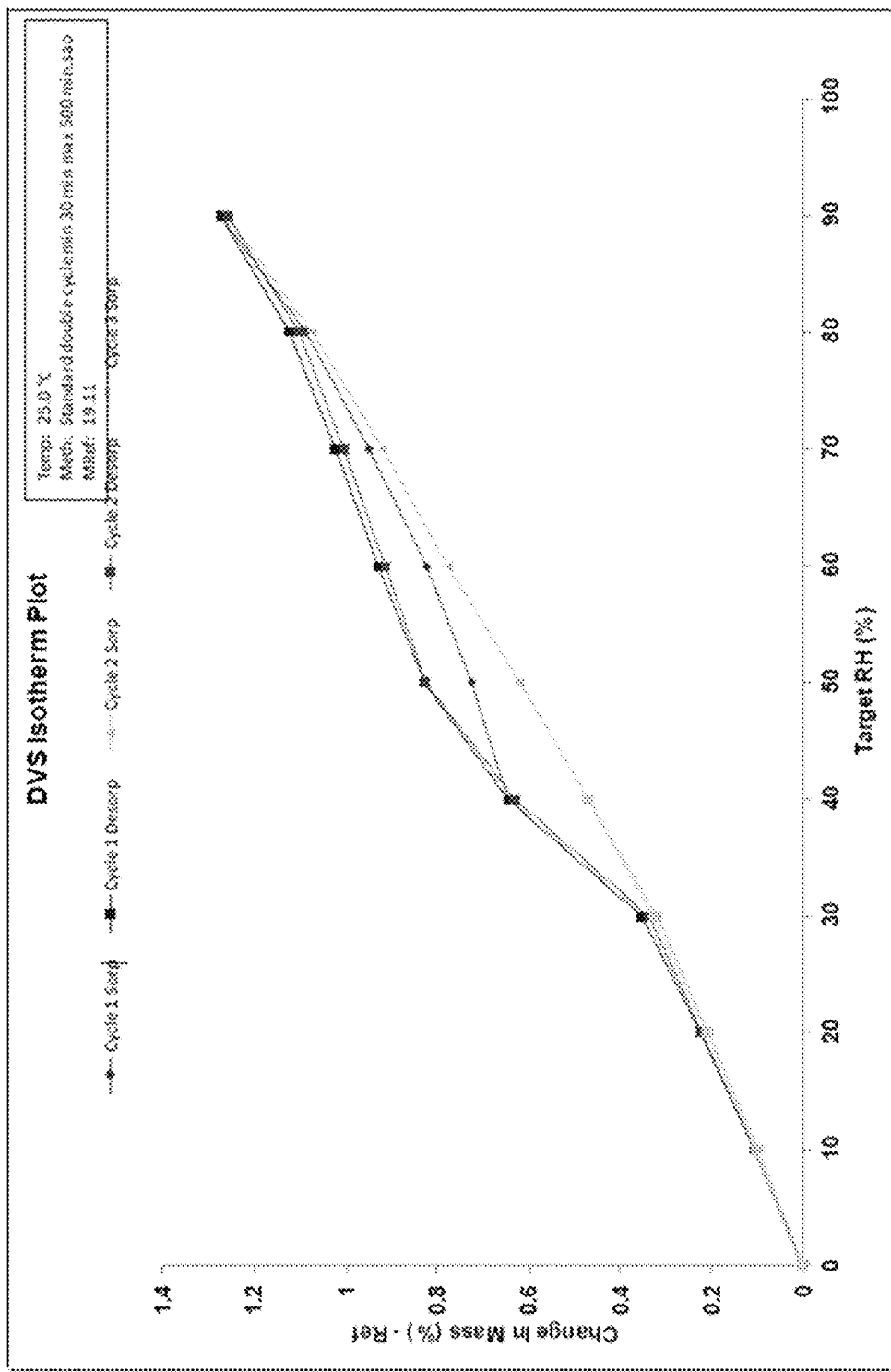
FIG. 4 presents the Dynamic Vapor Sorption isoform plot of anhydrous Form I carried out on a balance by Surface Measurement Systems with relatively humidity ramping at 10% increments

Dynamic vapor sorption studies of Form I showed that this novel polymorphic form is non-hygroscopic, with a mass uptake of approximately 0.9% at 90% relative humidity, as shown in FIG. 4. No form change was seen during DVS cycling or post-DVS, indicating this form is stable and not prone to water uptake, which presents a significant technical advantage in pharmaceutical composition processing, storage, stability, and maintained efficacy after long-term storage at ambient conditions.

Figure 5:
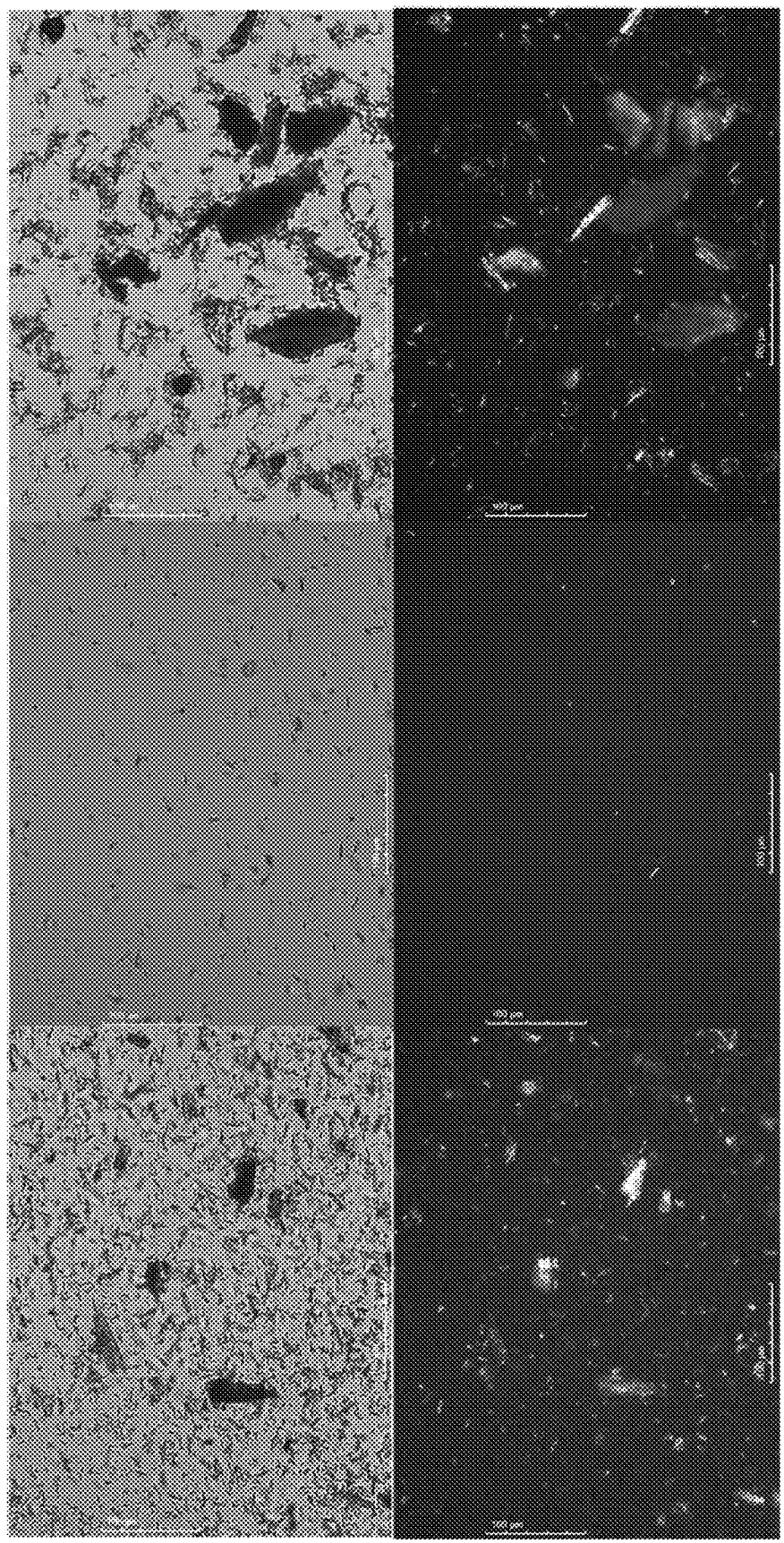
FIG. 5 presents the Polarised Light Microscopy images of anhydrous Form I imaged using an Olympus BX50 microscope equipped with cross-polarizing lenses.

Polymorphic Form I of Compound 1 was further characterized using polarized light microscopy. Form I displayed birefringent, rod-like morphology with limited agglomeration observed. The limited agglomeration provides beneficial characteristics for pharmaceutical compositions by improving the solubility of the compound. Representative images are displayed in FIG. 5.

In some embodiments, the present invention includes a novel crystalline form of 1-[2-[5-[(3-Methyl-3-oxetanyl) methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 7.1, 14.8, and 18.3. In another aspect, the crystalline form has additional peaks at diffraction angles (2Θ±0.2) 7.1, 14.8, 18.3, 24.3 and 26.9. In another aspect, the crystalline form has additional peaks at diffraction angles (2Θ±0.2) 7.1, 14.8, 16.0, 17.5, 18.2, 24.3, 25.3, and 26.9. In another aspect, the crystalline form has additional peaks at diffraction angles (2Θ±0.2) 7.1, 14.8, 16.0, 16.8, 17.5, 18.2, 19.7, 21.4, 24.3, 25.3, and 26.9. In another aspect, the crystalline form has additional peaks at diffraction angles (2Θ±0.2) 7.1, 8.0, 9.6, 11.4, 11.8, 13.9, 14.5, 14.8, 15.5, 16.0, 16.3, 16.8, 17.5, 18.2, 18.7, 19.3, 19.6, 19.7, 20.0, 20.3, 20.9, 21.4, 21.8, 22.6, 24.3, 25.3, 25.9, 26.9, 28.1, 29.5, 29.9, 31.0, 32.3, 33.4, and 34.3. In another aspect, the crystalline form is anhydrous. In a further aspect, the crystalline form has a melting point onset of 264° C. In another aspect, the crystalline form has a FT-IR spectrum comprising peaks at about 1479, 1271, 1185, 1033, 824, 751, 728, 690, 612, and 564 cm⁻¹. In another aspect, the crystalline form is non-hygroscopic. In another aspect, the crystalline form has a mass uptake of about 0.9% at 90% RH. In a further aspect, the crystalline form has birefringent, rod-like morphology by polarized light microscopy. In another aspect, the crystalline form is substantially pure.

In other embodiments, the present invention includes a process for the preparation of a crystalline form comprising suspending 1-[2-[5-[(3-Methyl-3-oxetanyl)methoxy]-1H-benzimidazol-1-yl]-8-quinolinyl]-4-piperidinamine monobenzenesulfonate in 1,1-dimethoxymethane or 1-butanol; and then stirring or shaking until precipitation.

Polymorphic Form II

Polymorphic Form II of Compound 1 is a hemi-hydrate crystalline form of the besylate salt. Methods for producing Compound 1 are detailed in U.S. Pat. No. 7,183,414. Polymorphic Form II was produced by slurrying the amorphous form of the besylate salt of Compound 1 in 98.5% ethanol/ 1.5% water (% v/v), by adding approximately 5 volumes of solvent to 10 mg of amorphous Compound 1, with shaking under ambient conditions. The slurry was then matured using thermal cycling, using 4-hour cycles of ambient and 40° C. temperatures for approximately 24 hours, after which the solids were isolated via centrifugation and dried for 24 hours in a 40° C. oven. XRPD analysis after initial solubility screening, of the wet solid post-thermal cycling maturation, and of the dried solid confirmed that Polymorph Form II was present.

Form II has several unexpected advantages over the amorphous form and other polymorphic forms identified herein. As a hemi-hydrate, it has better solubility in aqueous solutions (Form II is more soluble in aqueous solutions at neutral pH than the anhydrous Forms I and III), which makes Form II potentially more suitable for formulations such as oral liquid or topical solutions. Patients with oral sores related to mucositis, gastrointestinal issues, or patients uncomfortable or unable to swallow tablets or capsules for other reasons may benefit from oral suspension solutions.

Figure 6:
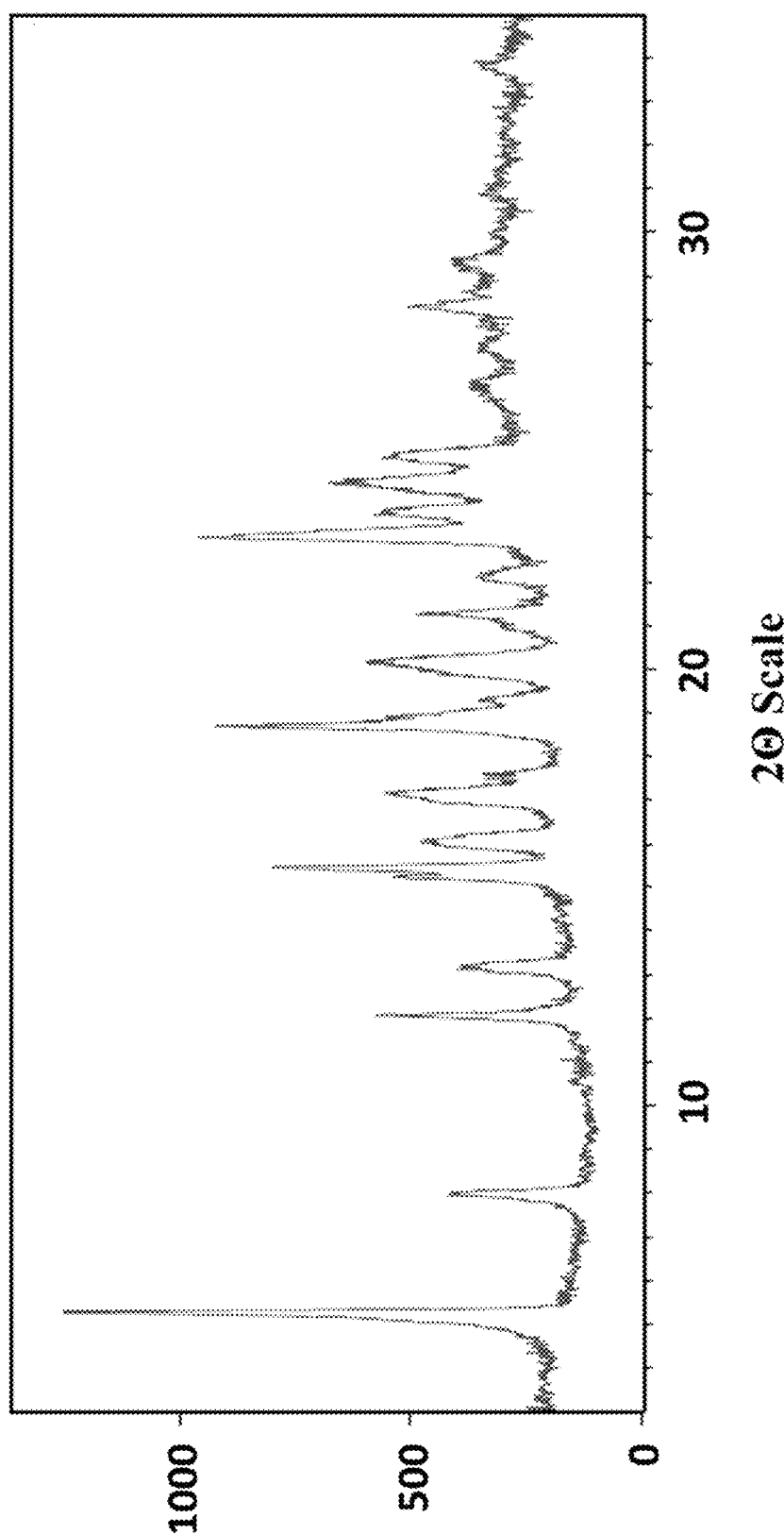
FIG. 6 presents the X-ray powder diffraction pattern of hemi-hydrate Form II carried out on a PANalytical X'pert pro with PIXcel detector.

Crystalline Form II was characterized by the XRPD pattern shown in FIG. 6. Table 4 shows the position of the peaks (expressed as 2Θ) and relative intensity, of the XPRD pattern for Form II as measured on a PANAlytical X'pert Pro with CuK radiation as detailed herein.

TABLE 3

| Angle (Degree 2Θ) | Relative Intensity (%) |
| --- | --- |
| 3.3 | 1.88 |
| 3.5 | 1.35 |
| 3.8 | 1.16 |
| 5.3 | 100 |
| 6.1 | 2.38 |
| 6.4 | 0.87 |
| 8.0 | 19.41 |
| 8.5 | 0.87 |
| 8.8 | 1.73 |
| 8.9 | 1.66 |
| 9.6 | 1.4 |
| 10.5 | 1.83 |
| 11.1 | 0.96 |
| 11.5 | 1.98 |
| 12.4 | 3.48 |
| 12.8 | 36.96 |
| 13.1 | 16.84 |
| 13.3 | 16.51 |
| 13.7 | 0.91 |
| 14.0 | 1.91 |
| 14.2 | 1.43 |
| 14.5 | 0.77 |
| 15.2 | 31.03 |

TABLE 3-continued

| Angle (Degree 2Θ) | Relative Intensity (%) |
|---|---|
| 15.5 | 54.18 |
| 15.9 | 18.12 |
| 16.2 | 15.1 |
| 17.0 | 21.3 |
| 17.2 | 28.07 |
| 17.6 | 10.61 |
| 18.1 | 1.95 |
| 18.7 | 63.91 |
| 19.3 | 10.17 |
| 19.8 | 14.43 |
| 20.3 | 24.32 |
| 20.9 | 6.89 |
| 21.3 | 22.36 |
| 22.0 | 8.87 |
| 23.0 | 59.54 |
| 23.5 | 23.22 |
| 23.7 | 18.96 |
| 24.2 | 30.51 |
| 25.0 | 19.5 |
| 25.6 | 10.74 |
| 25.8 | 1.28 |
| 26.4 | 4.64 |
| 26.6 | 5.48 |
| 27.4 | 3.11 |
| 28.3 | 15.42 |
| 28.6 | 5.34 |
| 29.1 | 7.21 |
| 29.4 | 4.76 |
| 30.9 | 4.85 |
| 31.5 | 1.83 |
| 31.7 | 1.37 |
| 31.9 | 1.71 |
| 32.0 | 2.7 |
| 32.2 | 2.09 |
| 32.8 | 4.85 |
| 33.8 | 7.22 |
| 34.8 | 1.7 |
| 39.9 | 1.98 |

Figure 7:
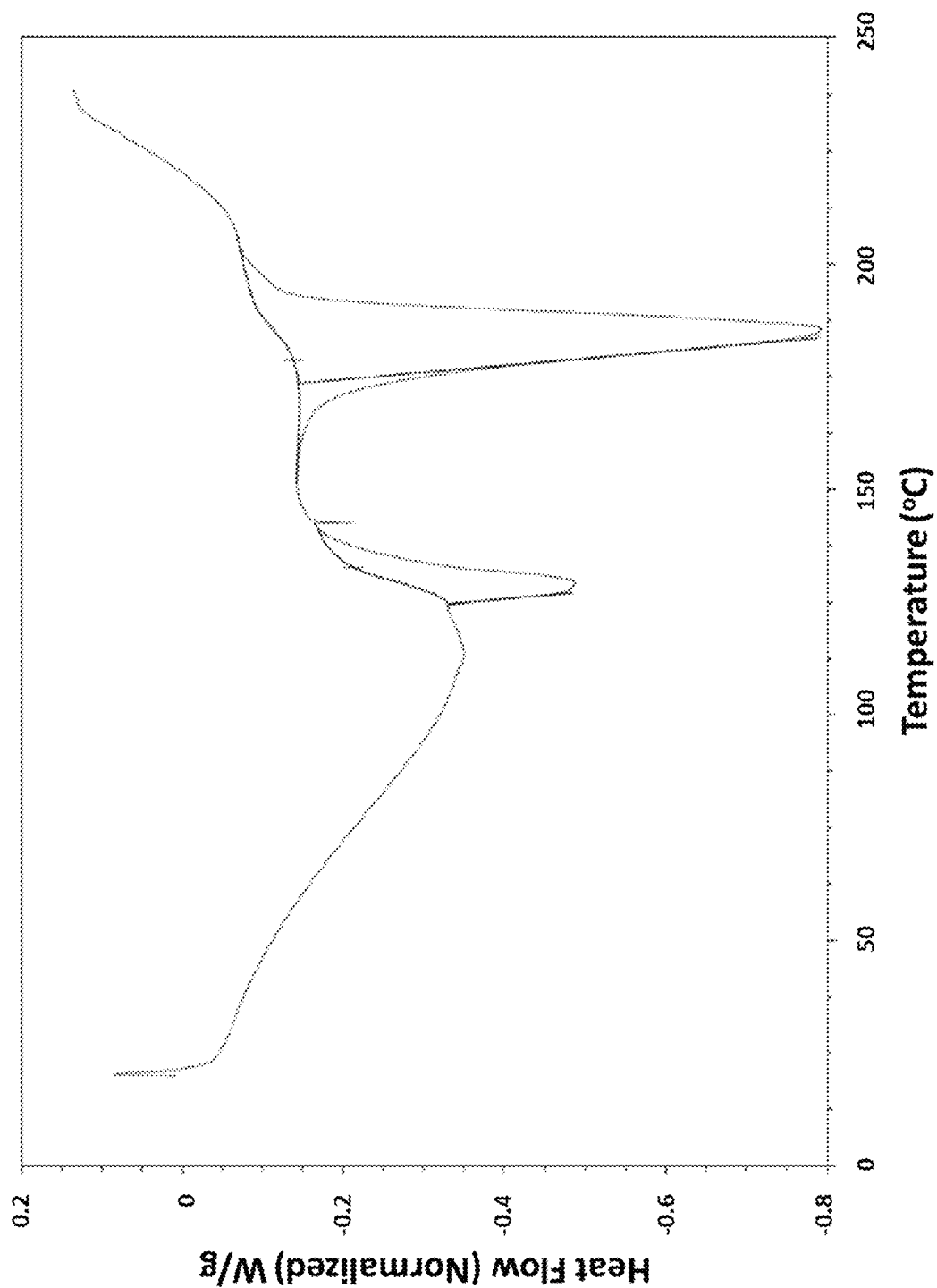
FIG. 7 presents a DSC thermogram of hemi-hydrate Form II carried out on a TA Instruments Discover DSC 250 differential scanning calorimeter equipped with a RC90 cooler using a heating rate of 10° C./min.

Crystalline Form II was also characterized by DSC (FIG. 7). TGA/DSC showed a large endothermic event with onset at 124° C. and peak at 130° C. followed by a large endothermic event with onset of 174° C. with a peak at 186° C., associated with loss of water and a decomposition event, respectively. Thermal degradation was observed with an onset of 165° C. Melt and degradation was associated with a 2.8% mass loss as measured by TGA, related to the loss of 0.7 equivalents of water. The observed degradation point of Form II was significantly lower than that of Form I, indicating that it is less stable.

Figure 8:
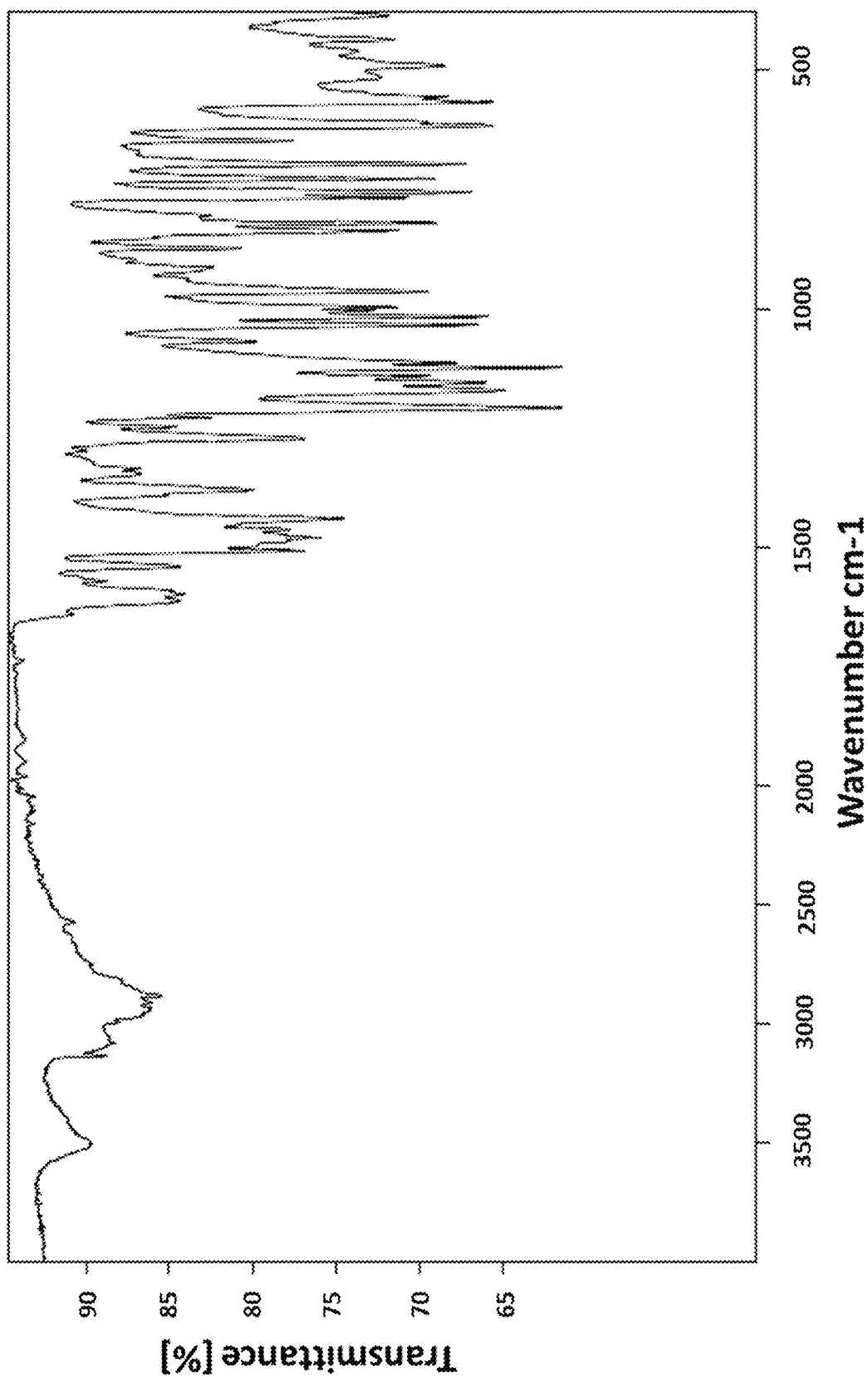
FIG. 8 presents the Fourier Transformed Infrared Spectroscopy spectrum of hemi-hydrate Form II carried out on a Bruker ALPHA P spectrometer.

Infrared spectrometry (FT-IR) was used to further characterize Form II of Compound 1. FIG. 8 shows the FT-IR spectra of Form II. The complete list of peak positions presented as wavenumber (cm$^{-1}$) and their relative intensity is included in Table 4.

TABLE 4

| Wavenumber (cm$^{-1}$) | Relative Intensity |
|---|---|
| 2952 | 0.004 |
| 2866 | 0.019 |
| 1645 | 0.003 |
| 1595 | 0.015 |
| 1565 | 0.005 |
| 1509 | 0.030 |
| 1480 | 0.059 |
| 1441 | 0.038 |
| 1385 | 0.020 |
| 1334 | 0.015 |
| 1275 | 0.031 |
| 1251 | 0.011 |
| 1229 | 0.010 |
| 1203 | 0.008 |
| 1187 | 0.082 |
| 1169 | 0.013 |
| 1155 | 0.028 |
| 1140 | 0.021 |
| 1124 | 0.047 |
| 1069 | 0.012 |
| 1052 | 0.008 |
| 1033 | 0.037 |
| 1016 | 0.071 |
| 996 | 0.014 |
| 954 | 0.038 |
| 909 | 0.021 |
| 860 | 0.012 |
| 850 | 0.007 |
| 831 | 0.007 |
| 821 | 0.060 |
| 799 | 0.046 |
| 758 | 0.011 |
| 750 | 0.059 |
| 728 | 0.073 |
| 693 | 0.048 |
| 640 | 0.022 |
| 613 | 0.128 |
| 563 | 0.059 |
| 516 | 0.018 |

Figure 9:
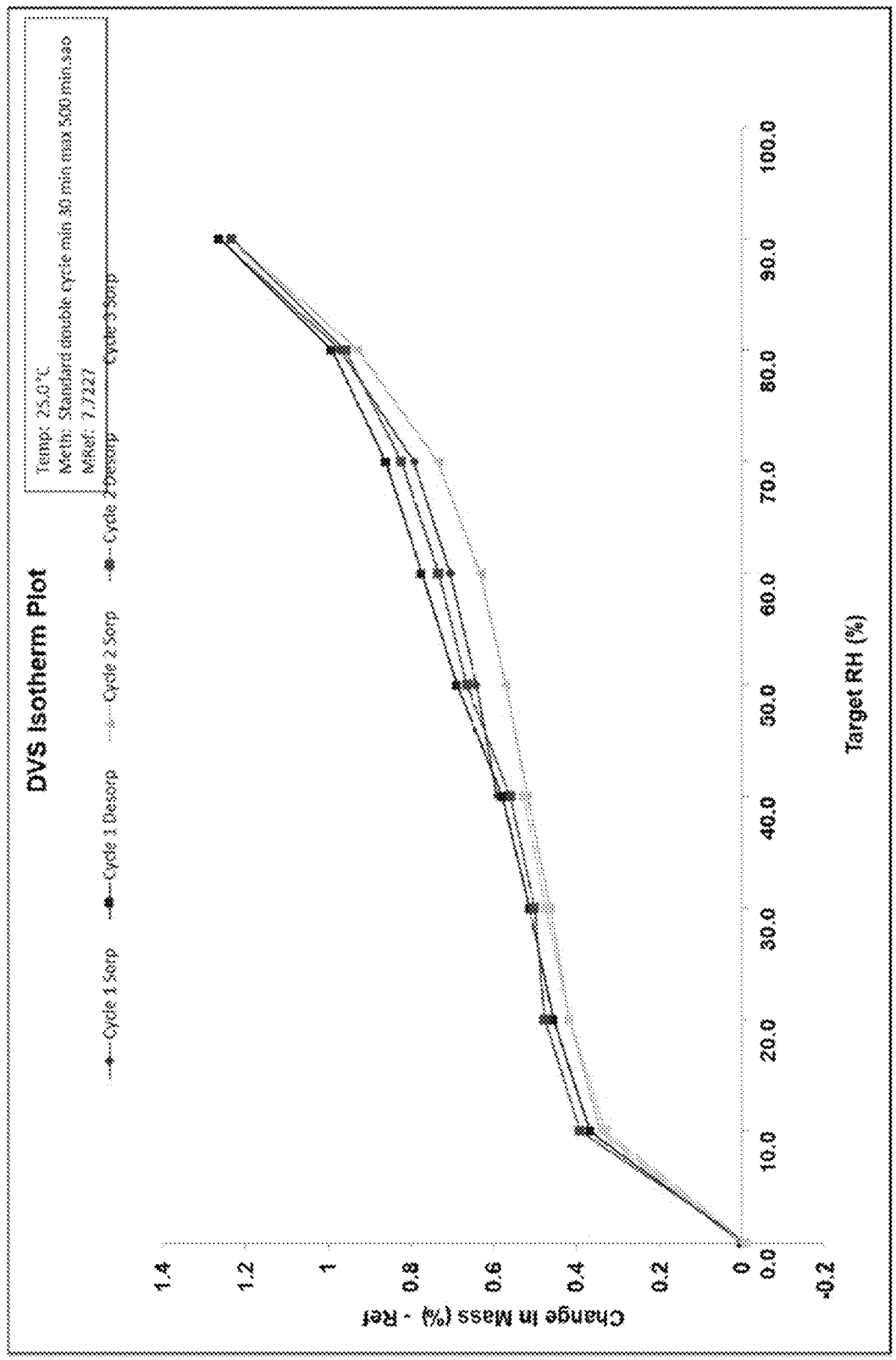
FIG. 9 presents the Dynamic Vapor Sorption isoform plot of anhydrous Form II carried out on a balance by Surface Measurement Systems with relatively humidity ramping at 10% increments

Dynamic vapor sorption studies of Form II showed that this novel polymorphic form is slightly hygroscopic, with a mass uptake of approximately 1.5% at 90% relative humidity, as shown in FIG. 9. No form change was seen during DVS cycling, indicating this form is stable and not prone to water uptake, which presents a significant technical advantage in pharmaceutical composition processing, storage, stability, and maintained efficacy after long-term storage at ambient conditions.

Figure 10:
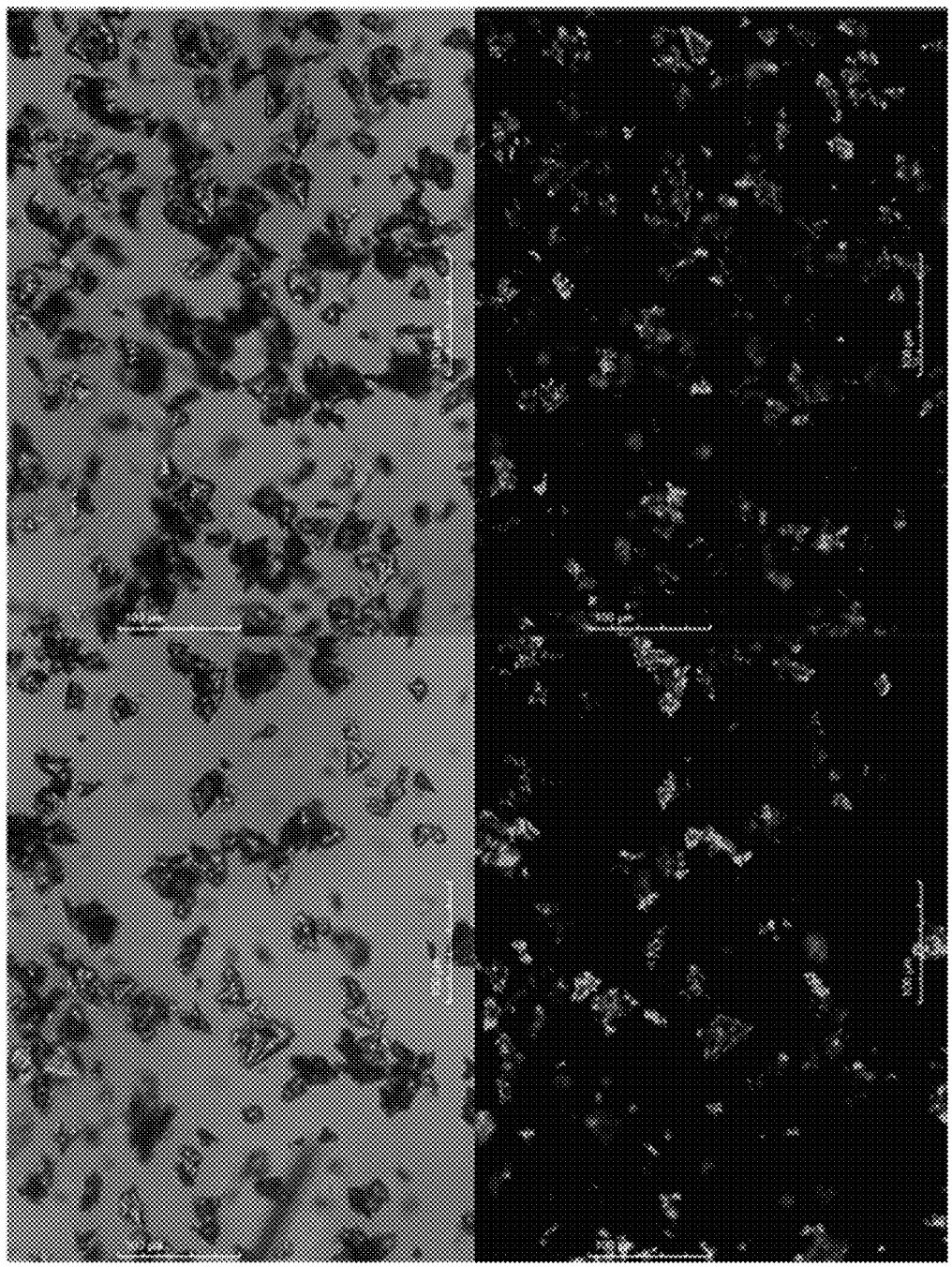
FIG. 10 presents the Polarised Light Microscopy images of hemi-hydrate Form II imaged using an Olympus BX50 microscope equipped with cross-polarizing lenses.

Polymorphic Form II of Compound 1 was further characterized using polarized light microscopy. Form II displayed small, highly birefringent, flakes with a prism like morphology. The limited agglomeration provides beneficial characteristics for pharmaceutical compositions by improving the solubility of the compound. Representative images are displayed in FIG. 10.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 5.3, 18.7, and 23.0. In another aspect, the crystalline form powder x-ray diffraction pattern has additional peaks at diffraction angles (2Θ±0.2) 5.3, 12.8, 15.5, 18.7, and 23.0. In another aspect, the crystalline form powder x-ray diffraction pattern has additional peaks at diffraction angles (2Θ±0.2) 5.3, 12.8, 15.2, 15.5, 18.7, 23.0, and 24.2. In another aspect, the crystalline form powder x-ray diffraction pattern has additional peaks at diffraction angles (2Θ±0.2) 5.3, 12.8, 15.2, 15.5, 17.2, 18.7, 20.3, 23.0, 23.5 and 24.2. In another aspect, the crystalline form powder x-ray diffraction pattern has additional peaks at diffraction angles (2Θ±0.2) 3.3, 3.5, 3.8, 5.3, 6.1, 6.4, 8.0, 8.5, 8.8, 8.9, 9.6, 10.5, 11.1, 11.5, 12.4, 12.8, 13.1, 13.3, 13.7, 14.0, 14.2, 14.5, 15.9, 15.2, 15.5, 16.2, 17.0, 17.2, 17.6, 18.1, 18.7, 19.3, 19.8, 20.3, 20.9, 21.3, 22.0, 23.0, 23.5, 23.7, 24.2, 25.0, 25.6, 25.8, 26.4, 26.6, 27.4, 28.3, 28.6, 29.1, 29.4, 30.9, 31.5, 31.7, 31.9, 32.0, 32.2, 32.8, 33.8, 34.8, and 39.9. In another aspect, the crystalline form is a hemi-hydrate. In another aspect, the crystalline form has a melting point onset of about 174° C. In another aspect, the crystalline form has a FT-IR spectrum comprising peaks at about 1480, 1187, 1124, 1016, 821, 750, 728, 693, 613, and 563 cm$^{-1}$. In another aspect, the crystalline form is slightly hygroscopic. In another aspect, the crystalline form has a mass uptake of about 1.5% at 90% RH. In another aspect the crystalline form has highly birefringent rod-like morphology by polarized light microscopy. In another aspect the crystalline form is substantially pure.

In other embodiments, the present invention includes a process for the preparation of a crystalline form of Compound 1 comprising suspending 1-[2-[5-[(3-Methyl-3-oxetanyl)methoxy]-1H-benzimidazol-1-yl]-8-quinolinyl]-4-piperidinamine monobenzenesulfonate in 98.5% ethanol/ 1.5% water (% v/v); and then shaking until precipitation.

Polymorphic Form III

Polymorphic Form III of Compound 1 is an anhydrous crystalline form of the besylate salt. Methods for producing Compound 1 are detailed in U.S. Pat. No. 7,183,414. Polymorphic Form III was produced by slurrying the amorphous form of the besylate salt of Compound 1 in 99% ethanol/1% toluene (% v/v), by adding approximately 5 volumes of solvent to 10 mg of amorphous Compound 1, with shaking under ambient conditions. The slurry was then matured using thermal cycling, using 4-hour cycles of ambient and 40° C. temperatures for approximately 24 hours, after which the solids were isolated via centrifugation and dried for 24 hours in a 40° C. oven. XRPD analysis after initial solubility screening, of the wet solid post-thermal cycling maturation, and of the dried solid confirmed that Polymorph Form III was present.

Form III has several unexpected advantages over the amorphous form and other polymorphic forms identified herein. As an anhydrous form, Form III is not subject to the potential impurities that may be associated with solvated or hydrated form. In addition, Form III is the most thermodynamically stable crystalline form under competitive slurry conditions (i.e. Form I will convert to Form III when Form III seeds are present in a slurry). In addition, Form III has a higher temperature for onset of degradation than Form II. As an anhydrous form, Form III also has advantages over the hemi-hydrate Form II and solvated Form IV, both of which undergo form changes under certain environmental conditions, particularly desolvation followed by conversion to anhydrous crystalline forms.

Figure 11:
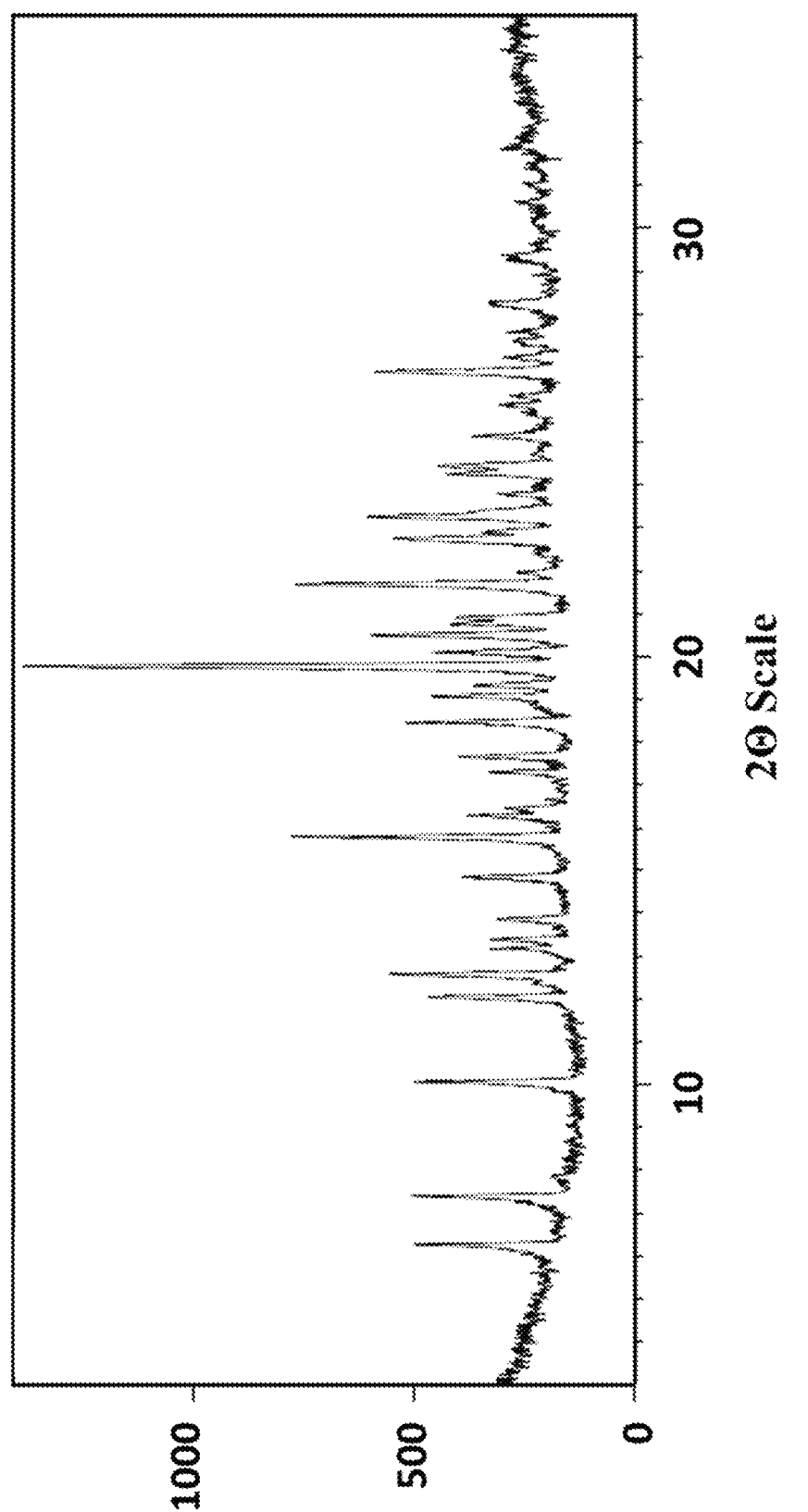
FIG. 11 presents the X-ray powder diffraction pattern of anhydrous Form III carried out on a PANalytical X'pert pro with PIXcel detector.

Crystalline Form III was characterized by the XRPD pattern shown in FIG. 11. Table 5 shows the position of the peaks (expressed as 2Θ) and relative intensity, of the XPRD pattern for Form III as measured on a PANAlytical X'pert Pro with CuK radiation as detailed herein.

TABLE 5

| Angle (Degree 2Θ) | Relative Intensity |
|---|---|
| 2.1 | 23.0 |
| 3.0 | 4.3 |
| 6.3 | 26.9 |
| 7.4 | 28.8 |
| 7.9 | 3.6 |
| 8.7 | 0.8 |
| 10.1 | 30.5 |
| 12.1 | 26.5 |
| 12.6 | 33.8 |
| 13.2 | 12.3 |
| 13.4 | 11.6 |
| 13.9 | 13.0 |
| 14.9 | 18.5 |
| 15.8 | 52.4 |

TABLE 5-continued

| Angle (Degree 2Θ) | Relative Intensity |
|---|---|
| 16.3 | 17.6 |
| 16.5 | 10.2 |
| 16.7 | 3.5 |
| 16.9 | 1.2 |
| 17.3 | 14.0 |
| 17.6 | 20.6 |
| 18.5 | 29.3 |
| 19.1 | 24.0 |
| 19.3 | 15.8 |
| 19.8 | 100.0 |
| 20.5 | 36.0 |
| 20.8 | 20.9 |
| 20.9 | 20.2 |
| 21.7 | 51.6 |
| 22.0 | 6.6 |
| 22.4 | 2.4 |
| 22.8 | 27.8 |
| 22.9 | 9.7 |
| 23.2 | 33.7 |
| 23.8 | 7.3 |
| 24.3 | 16.1 |
| 24.5 | 18.2 |
| 25.1 | 14.1 |
| 25.9 | 8.3 |
| 26.1 | 6.5 |
| 26.7 | 33.0 |
| 27.0 | 8.3 |
| 27.4 | 7.2 |
| 27.6 | 7.8 |
| 28.2 | 11.4 |
| 28.9 | 1.1 |
| 29.3 | 7.7 |
| 30.1 | 2.5 |
| 30.6 | 5.0 |
| 31.0 | 2.7 |
| 31.4 | 0.9 |
| 31.9 | 5.0 |

Figure 12:
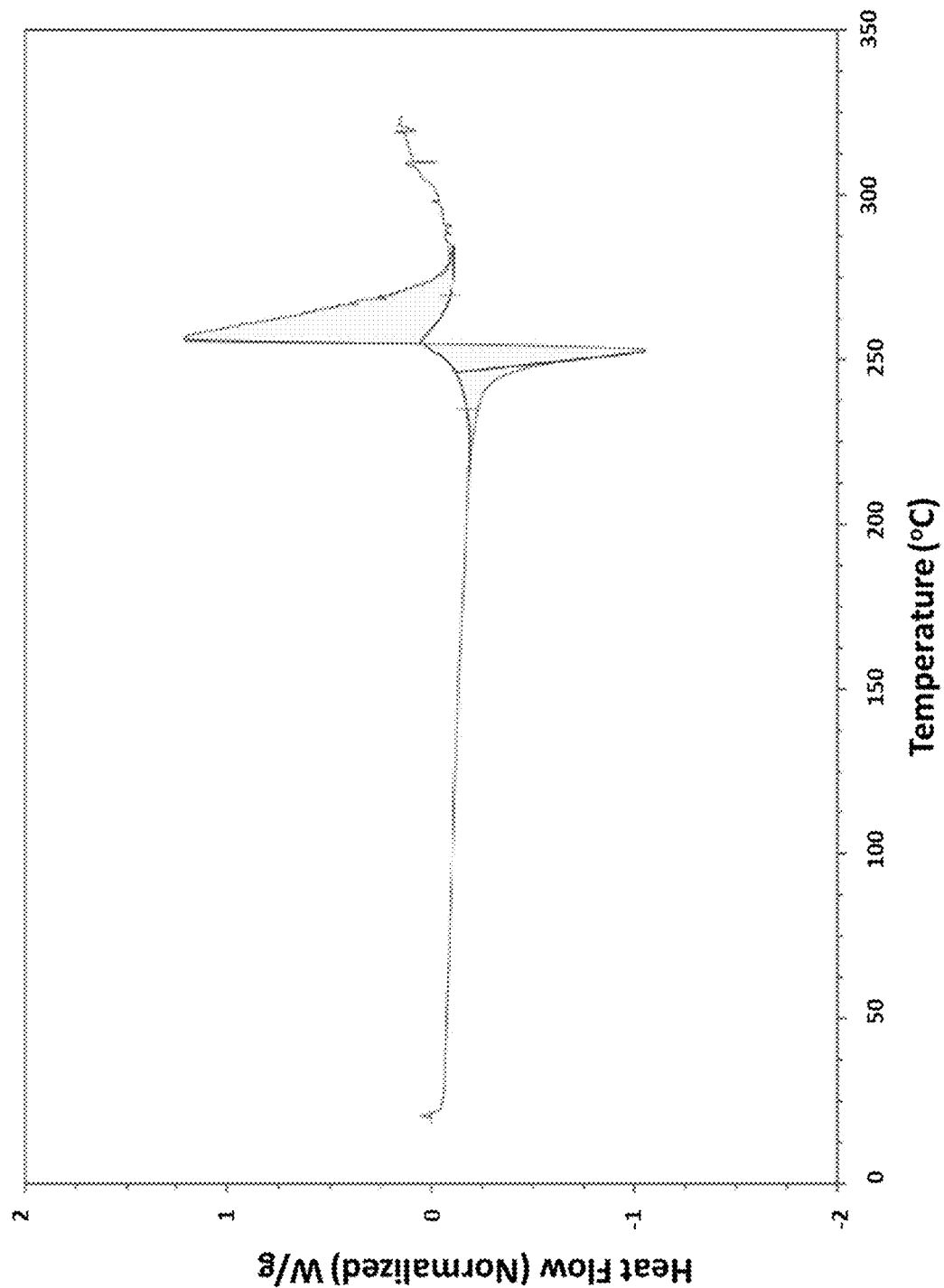
FIG. 12 presents a DSC thermogram of anhydrous Form III carried out on a TA Instruments Discover DSC 250 differential scanning calorimeter equipped with a RC90 cooler using a heating rate of 10° C./min.

Crystalline Form III was also characterized by DSC (FIG. 12). TGA/DSC showed a small endothermic event with onset at 251° C. and peak at 255° C. followed immediately by an exothermic event. Melt and degradation was associated with a 1.7% mass loss as measured by TGA, related to the loss of approximately 0.2 equivalents of excess ethanol. The observed degradation point of Form III was lower than that of Form I.

Figure 13:
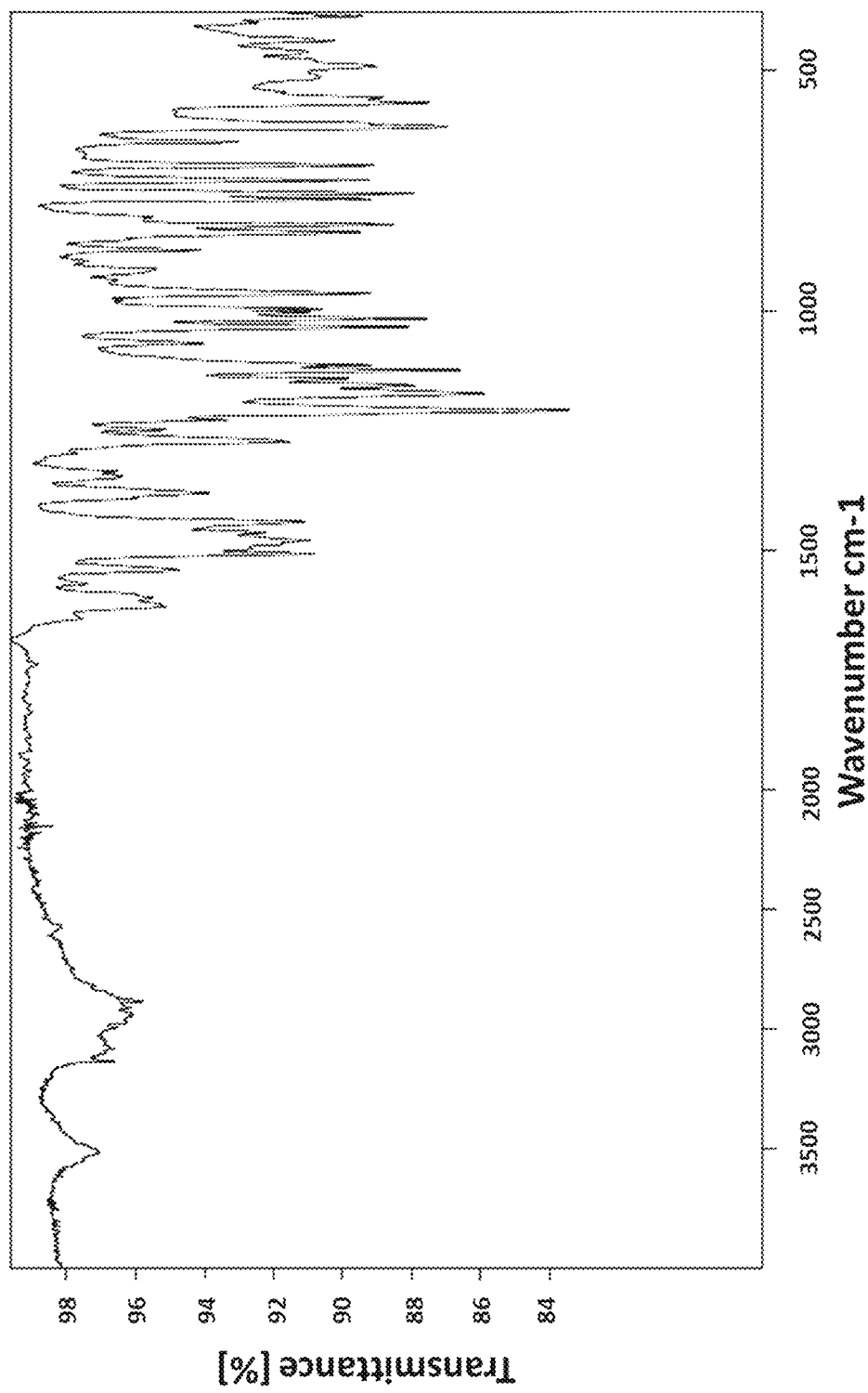
FIG. 13 presents the Fourier Transformed Infrared Spectroscopy spectrum of anhydrous Form III carried out on a Bruker ALPHA P spectrometer.

Infrared spectrometry (FT-IR) was used to further characterize Form III of Compound 1. FIG. 13 shows the FT-IR spectra of Form III. The complete list of peak positions presented as wavenumber (cm$^{-1}$) and their relative intensity is included in Table 6.

TABLE 6

| Wavenumber (cm$^{-1}$) | Relative Intensity |
|---|---|
| 2954 | 0.046 |
| 2888 | 0.010 |
| 2573 | 0.005 |
| 1645 | 0.010 |
| 1614 | 0.041 |
| 1601 | 0.014 |
| 1564 | 0.013 |
| 1509 | 0.116 |
| 1482 | 0.054 |
| 1461 | 0.021 |
| 1440 | 0.062 |
| 1400 | 0.021 |
| 1378 | 0.039 |
| 1334 | 0.048 |
| 1277 | 0.067 |
| 1251 | 0.024 |
| 1230 | 0.049 |

TABLE 6-continued

| Wavenumber (cm$^{-1}$) | Relative Intensity |
|---|---|
| 1202 | 0.033 |
| 1189 | 0.010 |
| 1169 | 0.149 |
| 1154 | 0.026 |
| 1140 | 0.059 |
| 1124 | 0.052 |
| 1107 | 0.040 |
| 1069 | 0.029 |
| 1052 | 0.040 |
| 1033 | 0.050 |
| 1015 | 0.112 |
| 1003 | 0.006 |
| 996 | 0.040 |
| 954 | 0.097 |
| 909 | 0.056 |
| 860 | 0.021 |
| 850 | 0.028 |
| 831 | 0.019 |
| 821 | 0.138 |
| 799 | 0.096 |
| 759 | 0.033 |
| 749 | 0.122 |
| 728 | 0.148 |
| 693 | 0.087 |
| 640 | 0.067 |
| 613 | 0.211 |
| 562 | 0.102 |
| 518 | 0.039 |
| 485 | 0.032 |
| 464 | 0.020 |
| 453 | 0.007 |
| 432 | 0.053 |
| 411 | 0.006 |
| 401 | 0.010 |

Figure 14:
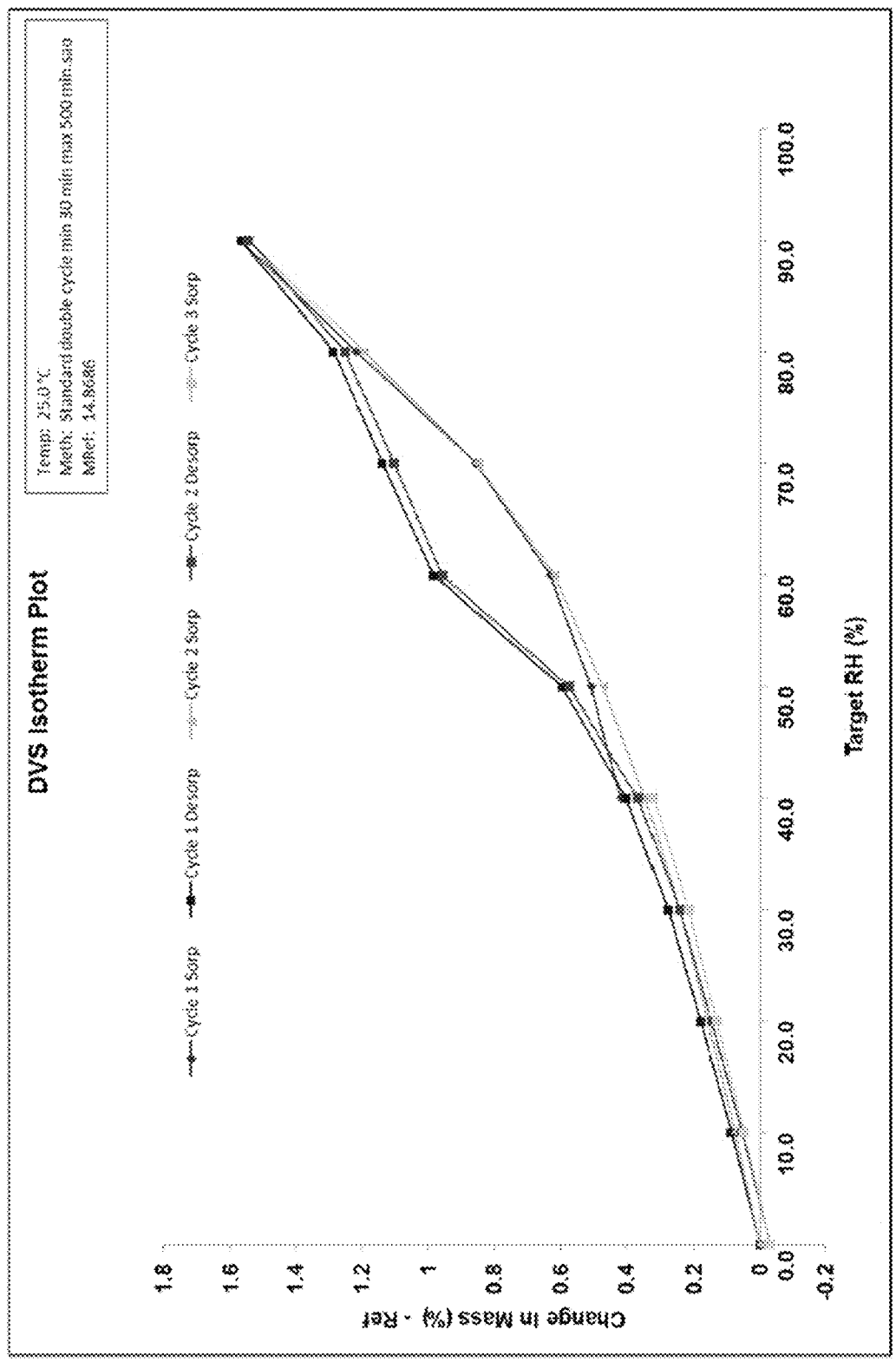
FIG. 14 presents the Dynamic Vapor Sorption isoform plot of anhydrous Form III carried out on a balance by Surface Measurement Systems with relatively humidity ramping at 10% increments.

Dynamic vapor sorption studies of Form III showed that this novel polymorphic form is slightly hygroscopic, with a mass uptake of approximately 1.5% at 90% relative humidity, as shown in FIG. 14. No form change was seen during DVS cycling, indicating this form is stable and not prone to water uptake, which presents a significant technical advantage in pharmaceutical composition processing, storage, stability, and maintained efficacy after long-term storage at ambient conditions.

Figure 15:
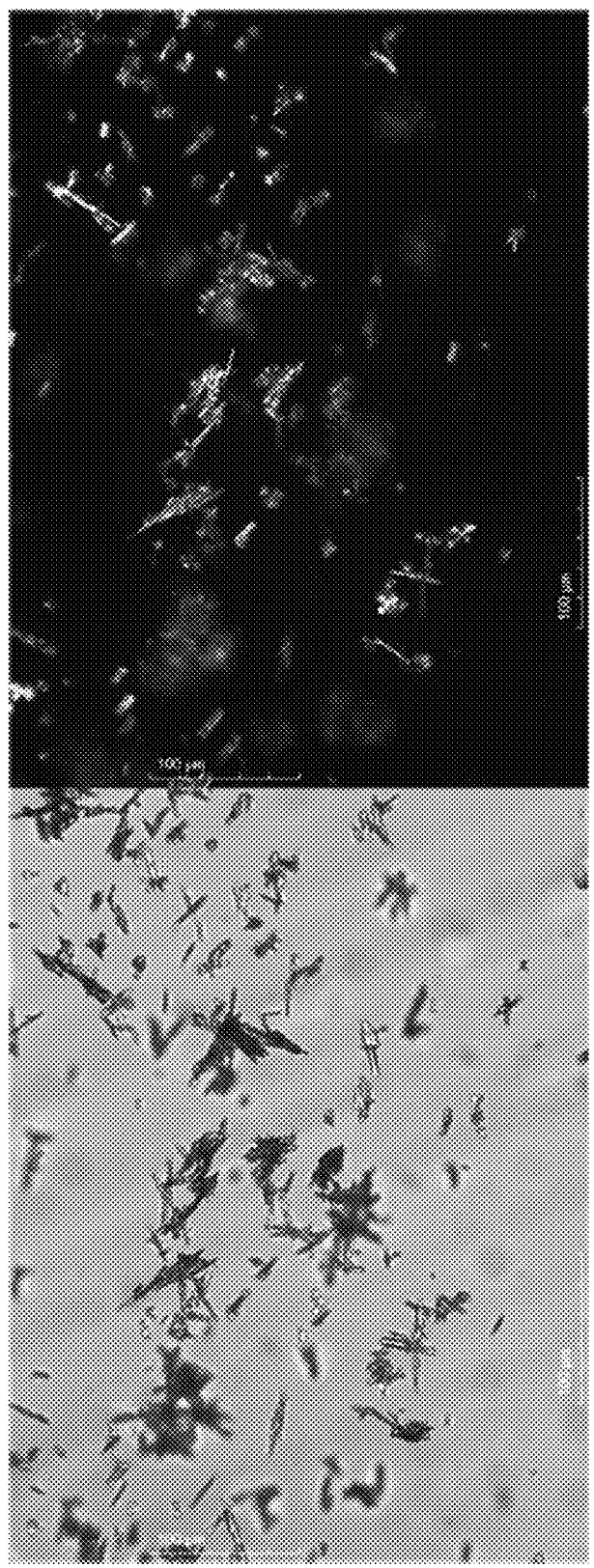
FIG. 15 presents the Polarised Light Microscopy images of anhydrous Form III imaged using an Olympus BX50 microscope equipped with cross-polarizing lenses.

Polymorphic Form III of Compound 1 was further characterized using polarized light microscopy. Form III displayed highly birefringent rod-like morphology. Representative images are displayed in FIG. 15.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 15.8, 19.8, and 21.7. In another aspect, the crystalline form powder x-ray diffraction pattern has additional peaks at diffraction angles (2Θ±0.2) 12.6, 15.8, 19.8, 20.5, and 21.7. In another aspect, the crystalline form powder x-ray diffraction pattern has additional peaks at diffraction angles (2Θ±0.2) 10.1, 12.6, 15.8, 19.8, 20.5, 21.7, 23.2, and 26.7. In another aspect, the crystalline form powder x-ray diffraction pattern has additional peaks at diffraction angles (2Θ±0.2) 7.4, 10.1, 12.6, 15.8, 18.5, 19.8, 20.5, 21.7, 22.8, 23.2, and 26.7. In another aspect, the crystalline form powder x-ray diffraction pattern has additional peaks at diffraction angles (2Θ±0.2) 2.1, 3.0, 6.3, 7.4, 7.9, 8.7, 10.1, 12.1, 12.6, 13.2, 13.4, 13.9, 14.9, 15.8, 16.3, 16.5, 16.7, 16.9, 17.3, 17.6, 18.5, 19.1, 19.3, 19.8, 20.5, 20.8, 20.9, 21.7, 22.0, 22.4, 22.8, 22.9, 23.2, 23.8, 24.3, 24.5, 25.1, 25.9, 26.1, 26.7, 27.0, 27.4, 27.6, 28.2, 28.9, 29.9, 30.1, 30.6, 31.0, 31.4, and 31.9. In another aspect, the crystalline form is anhydrous. In another aspect, the crystalline form has a melting point onset of about 251° C. In another aspect, the crystalline form has a FT-IR spectrum comprising peaks at about 1509, 1169, 1015, 954, 821, 799, 749, 728, 613, and 562 cm$^{-1}$. In another aspect, the crystalline form is slightly hygroscopic. In another aspect, the crystalline form has a mass uptake of about 1.5% at 90% RH. In another aspect, the crystalline form has highly birefringent rod-like morphology by polarized light microscopy. In another aspect, the crystalline form is substantially pure.

In other embodiments, the present invention includes a process for the preparation of a crystalline form of Compound 1 comprising suspending 1-[2-[5-[(3-Methyl-3-oxetanyl)methoxy]-1H-benzimidazol-1-yl]-8-quinolinyl]-4-piperidinamine monobenzenesulfonate in 99% ethanol/1% toluene (% v/v); and then shaking until precipitation.

Polymorphic Form IV

Polymorphic Form IV of Compound 1 is a solvated crystalline form of the besylate salt. Methods for producing Compound 1 are detailed in U.S. Pat. No. 7,183,414. Polymorphic Form IV was produced by slurrying the amorphous form of the besylate salt of Compound 1 in N,N'-dimethylacetamide by adding approximately 5 volumes of solvent to 10 mg of amorphous Compound 1, with shaking under ambient conditions. The slurry was then matured using thermal cycling, using 4-hour cycles of ambient and 40° C. temperatures for approximately 24 hours, after which the solids were isolated via centrifugation and dried for 24 hours in a 40° C. oven. XRPD analysis after initial solubility screening, of the wet solid post-thermal cycling maturation, and of the dried solid confirmed that only Polymorph Form IV was present. Form IV can also be obtained from slurrying Compound 1 in additional solvents including acetonitrile, butyl acetate, or ethanol, indicating that it may be an isostructural solvate.

Form IV has several unexpected advantages over the amorphous form and other polymorphic forms identified herein. As an isostructural solvate that can be obtained with ethanol, it may be suited to formulations requiring dissolution, such as oral suspensions or topical solutions using ethanol, or other pharmaceutical safe polar solvents such as glycerol, propylene glycol, or isopropyl alcohol. Patients with oral sores related to mucositis, gastrointestinal issues, or patients uncomfortable or unable to swallow tablets or capsules for other reasons may benefit from oral suspension solutions.

Figure 16:
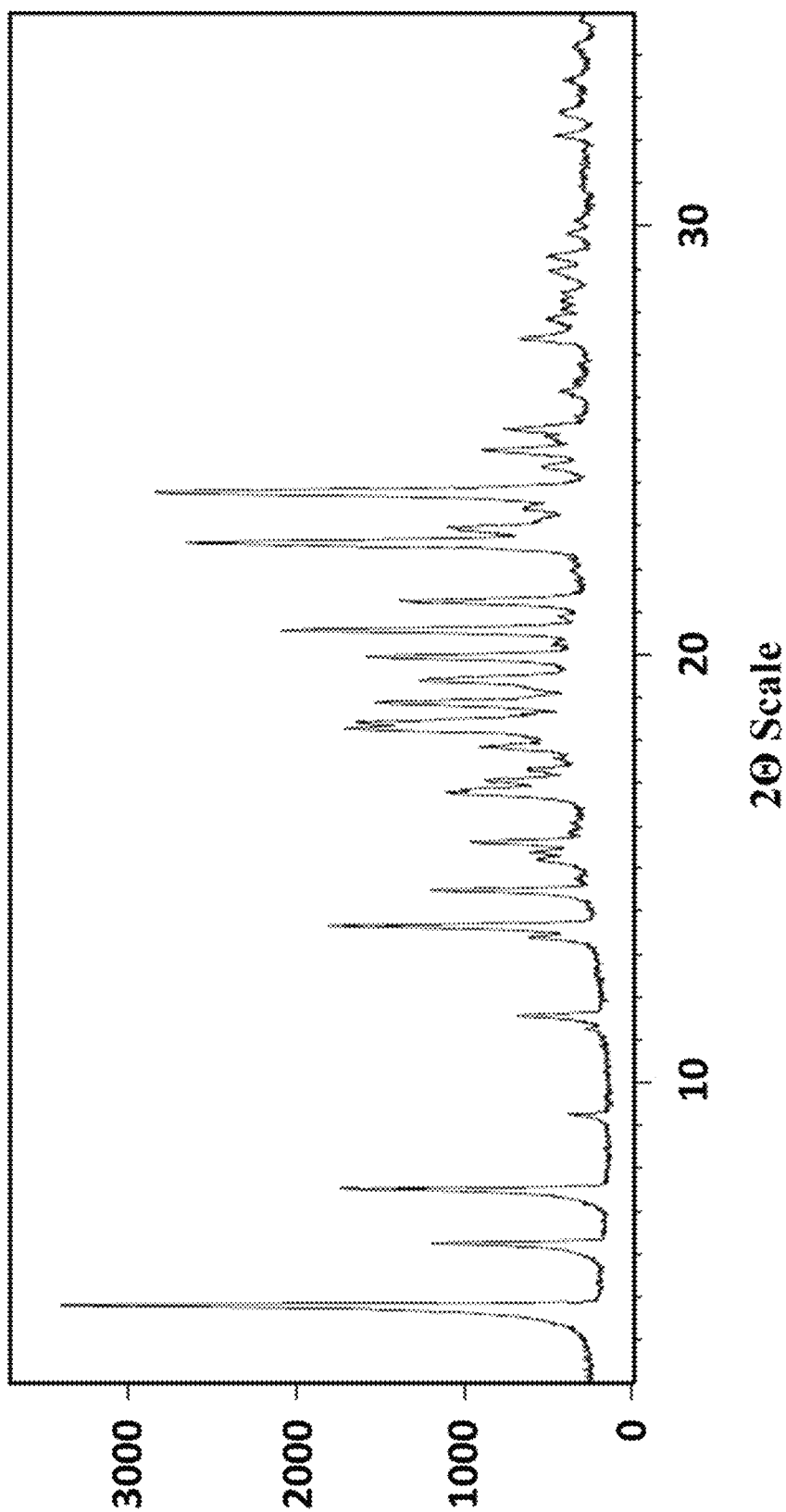
FIG. 16 presents the X-ray powder diffraction pattern of anhydrous Form IV carried out on a PANalytical X'pert pro with PIXcel detector.

Crystalline Form IV was characterized by the XRPD pattern shown in FIG. 16. Table 7 shows the position of the peaks (expressed as 2Θ) and relative intensity, of the XPRD pattern for Form IV as measured on a PANAlytical X'pert Pro with CuK radiation as detailed herein.

TABLE 7

| Angle (Degree 2Θ) | Relative Intensity |
|---|---|
| 4.8 | 100.0 |
| 6.3 | 29.5 |
| 7.5 | 44.8 |
| 9.3 | 6.5 |
| 11.6 | 14.8 |
| 13.4 | 8.7 |
| 13.7 | 46.2 |
| 14.5 | 27.0 |
| 15.2 | 6.0 |
| 15.4 | 7.0 |

TABLE 7-continued

| Angle (Degree 2Θ) | Relative Intensity |
|---|---|
| 15.6 | 19.4 |
| 16.7 | 20.5 |
| 17.3 | 5.7 |
| 17.8 | 12.2 |
| 18.2 | 34.1 |
| 18.4 | 33.8 |
| 18.9 | 32.0 |
| 19.4 | 25.4 |
| 20.0 | 34.1 |
| 20.2 | 1.7 |
| 20.6 | 50.6 |
| 20.9 | 2.2 |
| 21.3 | 28.3 |
| 22.6 | 64.3 |
| 22.9 | 20.8 |
| 23.8 | 72.8 |
| 24.4 | 5.5 |
| 24.8 | 16.5 |
| 25.3 | 12.3 |
| 26.2 | 3.8 |
| 27.4 | 10.9 |
| 27.8 | 4.0 |
| 28.1 | 2.8 |
| 28.3 | 2.9 |
| 28.4 | 2.8 |
| 28.9 | 5.3 |
| 29.3 | 5.49 |
| 29.8 | 2.71 |
| 31.0 | 0.63 |
| 32.1 | 5.35 |
| 32.6 | 3.74 |
| 33.3 | 2.01 |
| 34.2 | 2.34 |

Figure 17:
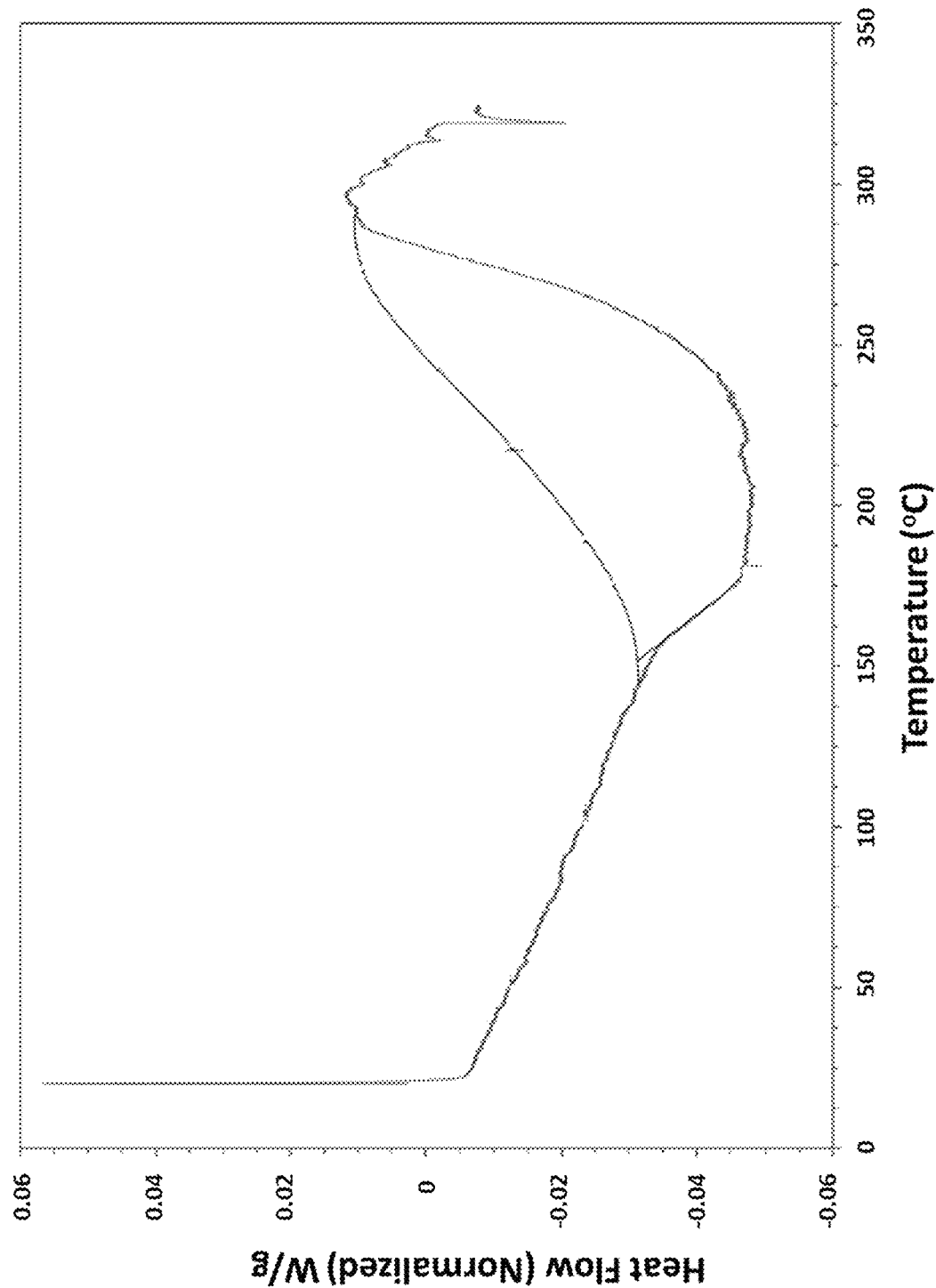
FIG. 17 presents a DSC thermogram of anhydrous Form IV carried out on a TA Instruments Discover DSC 250 differential scanning calorimeter equipped with a RC90 cooler using a heating rate of 10° C./min.

Crystalline Form IV was also characterized by DSC (FIG. 17). TGA/DSC showed a large very broad endothermic event at 144° C. related to desolvation followed by recrystallization observed starting at 182° C. A second large, very broad endothermic even with onset at 241° C. was related to a degradation even. Melt and degradation was associated with a 13.3% mass loss as measured by TGA, related to the loss of approximately 1 equivalent of DMA.

Figure 18:
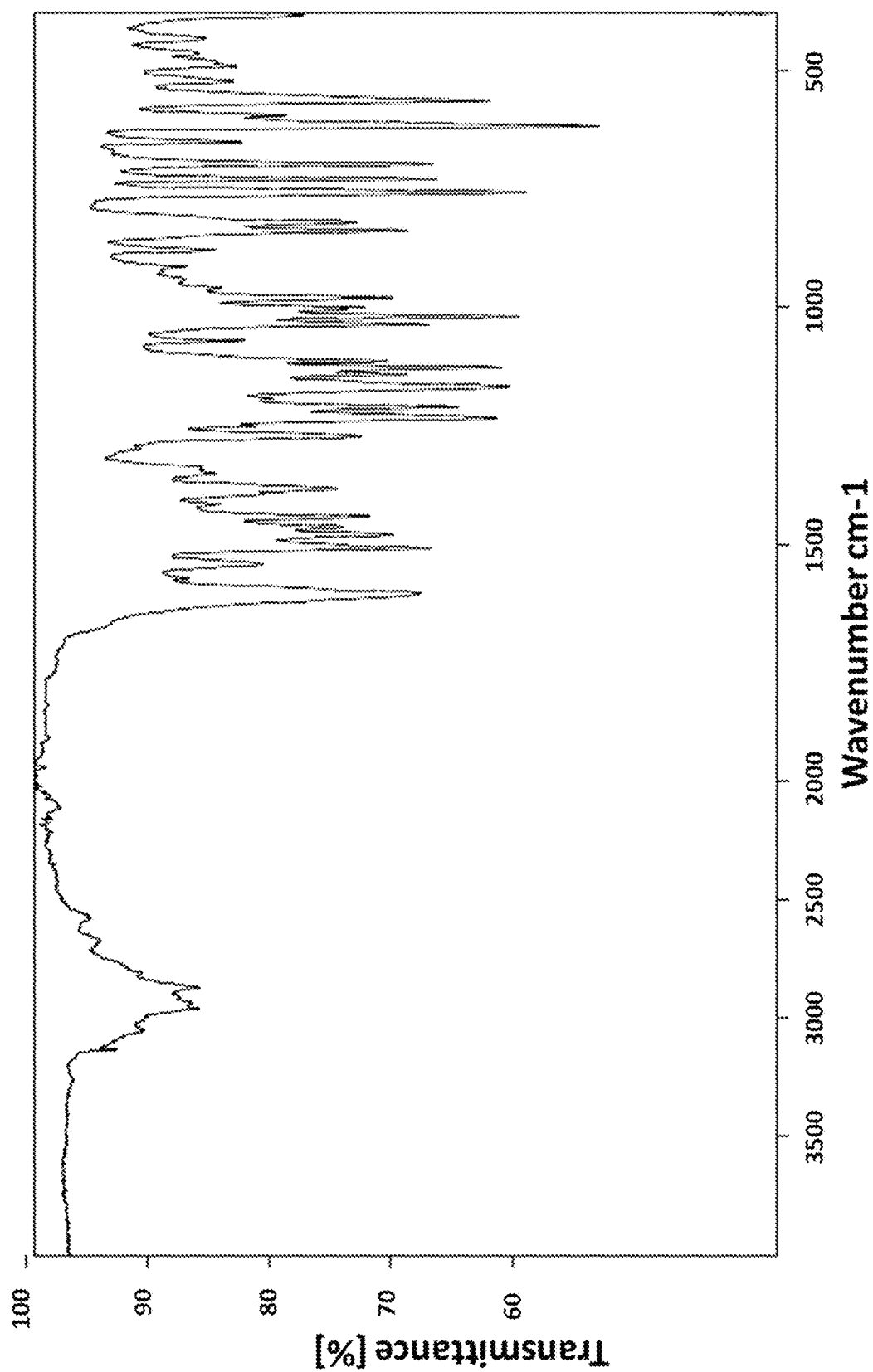
FIG. 18 presents the Fourier Transformed Infrared Spectroscopy spectrum of anhydrous Form IV carried out on a Bruker ALPHA P spectrometer.

Infrared spectrometry (FT-IR) was used to further characterize Form IV of Compound 1. FIG. 18 shows the FT-IR spectra of Form IV. The complete list of peak positions presented as wavenumber (cm$^{-1}$) and their relative intensity is included in Table 8.

TABLE 8

| Wavenumber (cm$^{-1}$) | Relative Intensity |
|---|---|
| 3050 | 0.012 |
| 2956 | 0.006 |
| 2933 | 0.021 |
| 2865 | 0.058 |
| 2799 | 0.018 |
| 2508 | 0.009 |
| 2127 | 0.015 |
| 1657 | 0.006 |
| 1600 | 0.047 |
| 1568 | 0.021 |
| 1540 | 0.022 |
| 1508 | 0.029 |
| 1498 | 0.014 |
| 1479 | 0.159 |
| 1468 | 0.020 |
| 1440 | 0.085 |
| 1384 | 0.081 |
| 1337 | 0.021 |
| 1272 | 0.117 |
| 1251 | 0.042 |
| 1226 | 0.027 |
| 1205 | 0.029 |
| 1184 | 0.220 |
| 1168 | 0.010 |
| 1154 | 0.056 |
| 1125 | 0.059 |
| 1113 | 0.102 |
| 1068 | 0.013 |
| 1033 | 0.144 |
| 1017 | 0.077 |
| 1009 | 0.009 |
| 998 | 0.024 |
| 984 | 0.048 |
| 953 | 0.010 |
| 941 | 0.010 |
| 921 | 0.033 |
| 880 | 0.007 |
| 858 | 0.047 |
| 833 | 0.015 |
| 824 | 0.143 |
| 794 | 0.076 |
| 751 | 0.140 |
| 728 | 0.130 |
| 713 | 0.011 |
| 690 | 0.114 |
| 647 | 0.057 |
| 612 | 0.791 |
| 564 | 0.131 |
| 510 | 0.025 |
| 483 | 0.052 |
| 448 | 0.058 |
| 405 | 0.011 |

Figure 19:
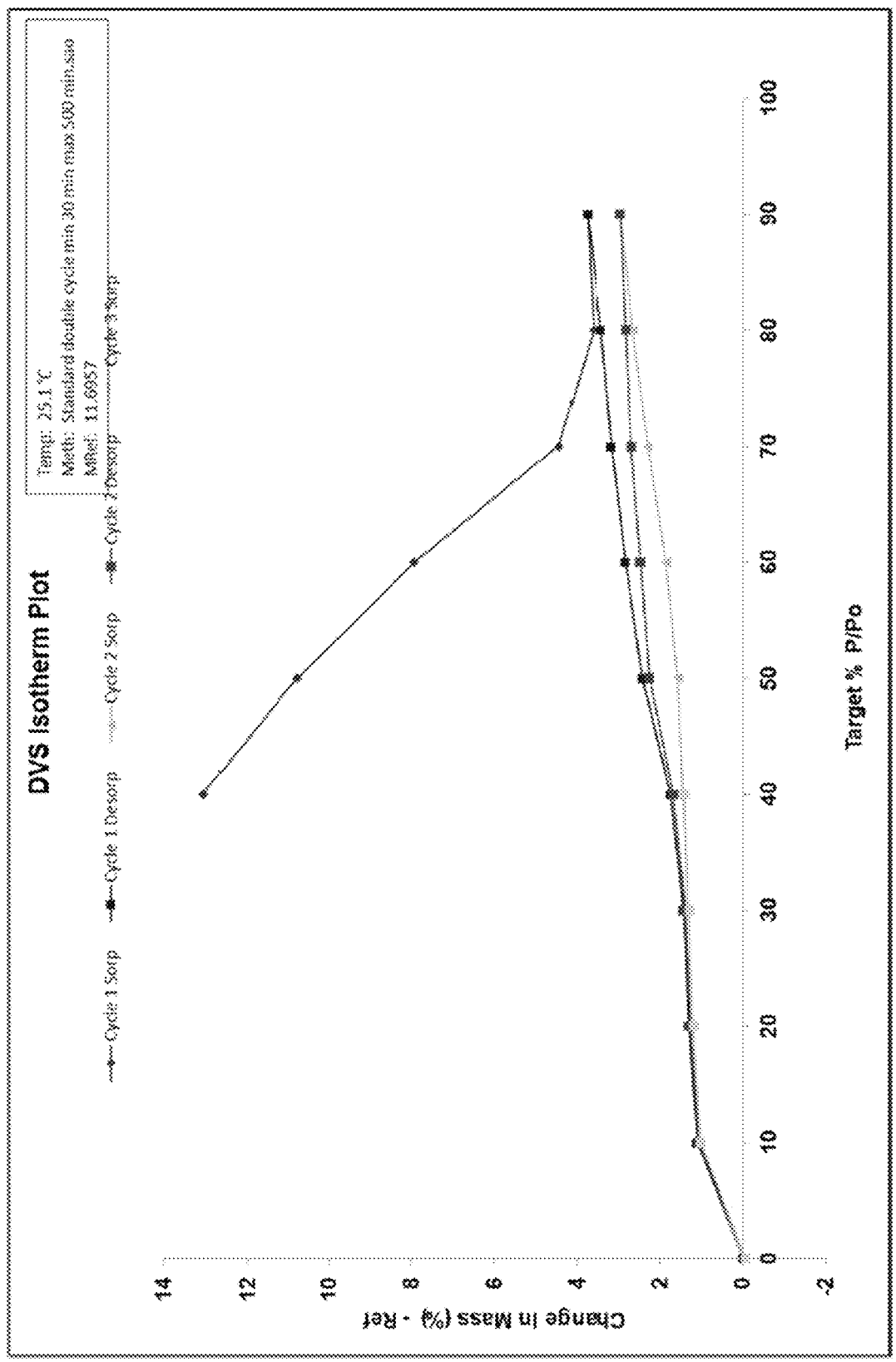
FIG. 19 presents the Dynamic Vapor Sorption isoform plot of anhydrous Form IV carried out on a balance by Surface Measurement Systems with relatively humidity ramping at 10% increments

Dynamic vapor sorption studies of Form IV showed that this novel polymorphic form desolvates, with a mass loss of 9.4% during the first cycle. The desolvated form was found to by hygroscopic, with a mass uptake of 1.5% between 0% and 10% humidity, as shown in FIG. 19. XPRD performed post-DVS cycling showed that Form IV converts to the hemi-hydrated Form II when exposed to high humidity.

Figure 20:
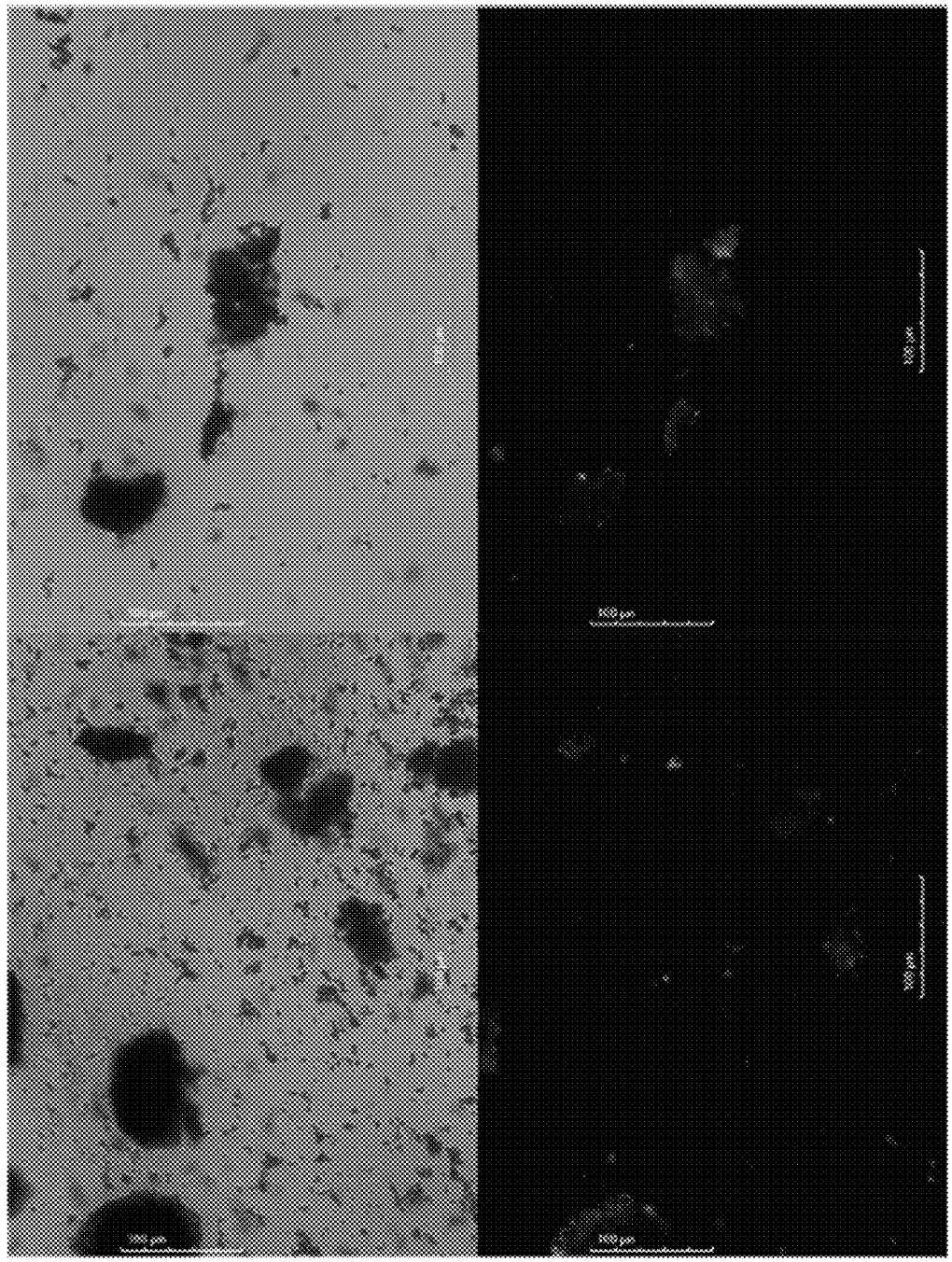
FIG. 20 presents the Polarised Light Microscopy images of anhydrous Form IV imaged using an Olympus BX50 microscope equipped with cross-polarizing lenses.

Polymorphic Form IV of Compound 1 was further characterized using polarized light microscopy. Form IV was slightly birefringent, with no defined morphology. Representative images are displayed in FIG. 20.

In other embodiments, the present invention includes a novel crystalline form of 1-[2-[5-[(3-Methyl-3-oxetanyl)methoxy]-1H-benzimidazol-1-yl]-8-quinolinyl]-4-piperidinamine monobenzenesulfonate wherein said crystalline form has a powder x-ray diffraction pattern comprising peaks at one or more of diffraction angles (2Θ±0.2) 4.8, 22.6, and 23.8. In another aspect, the crystalline form powder x-ray diffraction pattern has additional peaks at diffraction angles (2Θ±0.2) 4.8, 13.7, 20.6, 22.6, and 23.8. In another aspect, the crystalline form powder x-ray diffraction pattern has additional peaks at diffraction angles (2Θ±0.2) 4.8, 7.5, 13.7, 18.2, 20.6, 22.6, and 23.8. In another aspect, the crystalline form powder x-ray diffraction pattern has additional peaks at diffraction angles (2Θ±0.2) 4.8, 7.5, 13.7, 18.2, 18.4, 18.9, 20.0, 20.6, 22.6, and 23.8. In another aspect, the crystalline form powder x-ray diffraction pattern has additional peaks at diffraction angles (2Θ±0.2) 4.8, 6.3, 7.5, 9.3, 11.6, 13.4, 13.7, 14.5, 15.2, 15.4, 15.6, 16.7, 17.3, 17.8, 18.2, 18.4, 18.9, 19.4, 20.0, 20.2, 20.6, 20.9, 21.3, 22.6, 22.9, 23.8, 24.4, 24.8, 25.3, 26.2, 27.4, 27.8, 28.1, 28.3, 28.4, 28.9, 29.3, 29.8, 31.0, 32.1, 32.6, 33.3, and 34.2. In another aspect, the crystalline form is a solvate. In another aspect, the solvate form is a N,N'-dimethylacetamide solvate. In another aspect, the solvate form is an acetonitrile, butyl acetate, or ethanol solvate. In another aspect, the crystalline from has a degradation point onset of about 241° C. In another aspect, the crystalline form has a FT-IR spectrum comprising peaks at about 1479, 1272, 1184, 1033, 824, 751, 728, 690, 612, and 564 cm$^1$. In another aspect the crystalline form is hygroscopic. In another aspect, the crystalline form has a mass uptake of 1.5% between 0% and 10% RH. In another aspect, the crystalline form has weakly birefringent with no defined morphology by polarized light microscopy. In another aspect, the crystalline form is substantially pure.

In other embodiments, the present invention includes a process for the preparation of a crystalline of Compound 1 comprising suspending 1-[2-[5-[(3-Methyl-3-oxetanyl) methoxy]-1H-benzimidazol-1-yl]-8-quinolinyl]-4-piperidinamine monobenzenesulfonate in N,N'-dimethylacetamide, acetonitrile, butyl acetate, or ethanol; and then shaking until precipitation.

Amorphous Form

Figure 21:
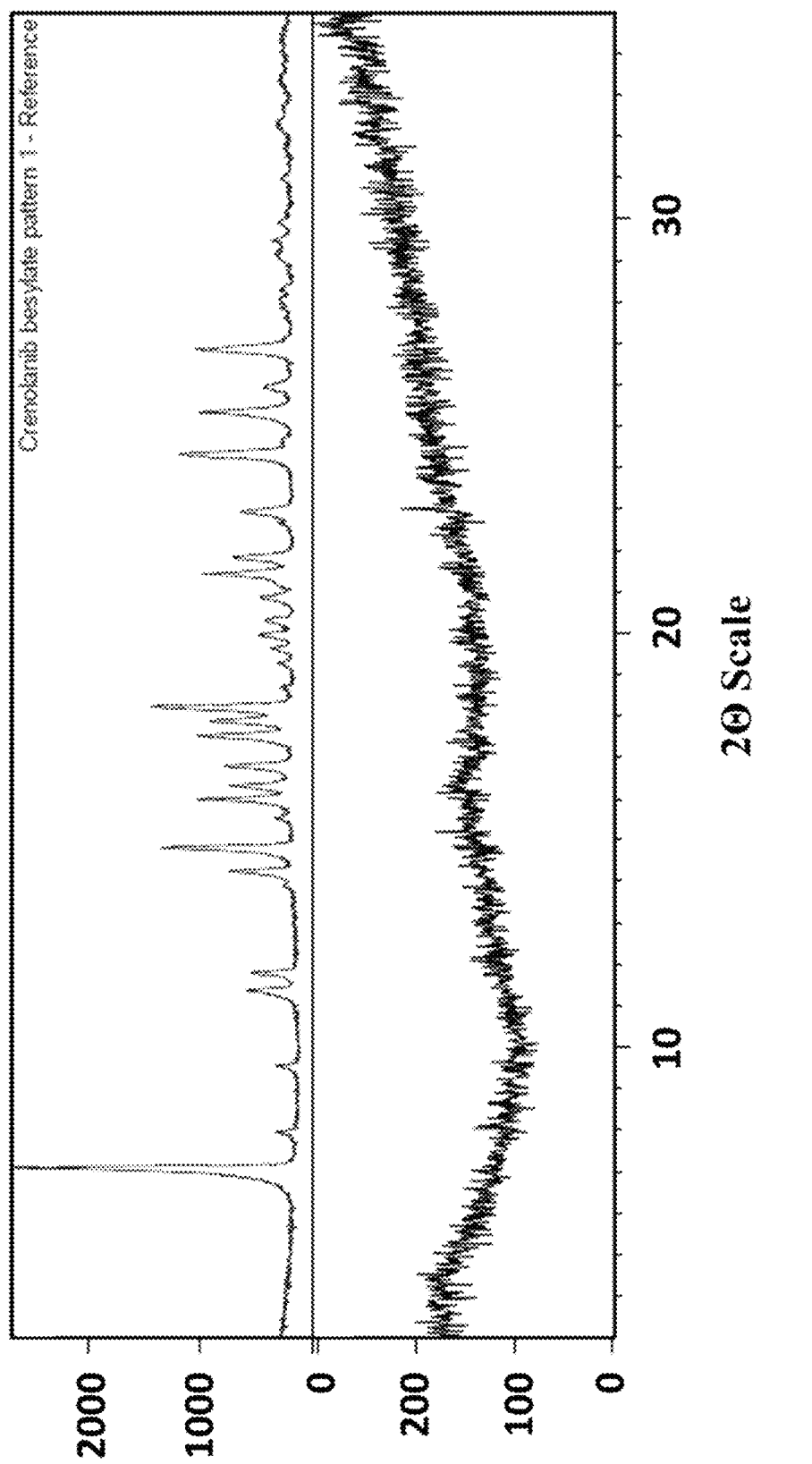
FIG. 21 presents the X-raw powder diffraction pattern of anhydrous Form I (top) and the amorphous form obtained from ethanol/water slurry (bottom) carried out on a PANalytical X'pert pro with PIXcel detector.

Methods for producing Compound 1 are detailed in U.S. Pat. No. 7,183,414. Amorphous Compound 1 was characterized by the XRPD pattern shown in FIG. 21.

In other embodiments, the present invention includes a solid form of 1-[2-[5-[(3-Methyl-3-oxetanyl)methoxy]-1H-benzimidazol-1-yl]-8-quinolinyl]-4-piperidinamine monobenzenesulfonate, wherein said form is amorphous.

In other embodiments, the present inventions includes a pharmaceutical composition comprising a crystalline form of 1-[2-[5-[(3-Methyl-3-oxetanyl)methoxy]-1H-benzimidazol-1-yl]-8-quinolinyl]-4-piperidinamine monobenzenesulfonate, its hydrates or solvates, and a pharmaceutically acceptable carrier.

In other embodiments, the present invention includes a method for the treatment of a subject suffering from a disease comprising administering a therapeutically effective amount of a crystalline form of Compound 1. In one aspect, the disease is a proliferative disorder. said proliferator disorder is selected from Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AMLITMDS), mixed lineage leukemia (MLL), myelodysplastic syndromes (MDS), myeloproliferative disorders (MPD), multiple myeloma, biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, uterine cancer, or other tumors.

REFERENCES

Heldin, C. H., J. Lennartsson and B. Westermark (2017). "Involvement of PDGF ligands and receptors in tumorigenesis." *J Intern Med.*

Lewis, N. L., L. D. Lewis, J. P. Eder, N. J. Reddy, F. Guo, K. J. Pierce, A. J. Olszanski and R. B. Cohen (2009). "Phase I study of the safety, tolerability, and pharmacokinetics of oral CP-868,596, a highly specific platelet-derived growth factor receptor tyrosine kinase inhibitor in patients with advanced cancers." *J Clin Oncol* 27(31): 5262-5269.

Smith, C. C., E. A. Lasater, K. C. Lin, Q. Wang, M. Q. McCreery, W. K. Stewart, L. E. Damon, A. E. Perl, G. R. Jeschke, M. Sugita, M. Carroll, S. C. Kogan, J. Kuriyan and N. P. Shah (2014). "Crenolanib is a selective type I pan-FLT3 inhibitor." *Proc Natl Acad Sci USA* 111(14): 5319-5324.

Tsioumpekou, M., S. I. Cunha, H. Ma, A. Ahgren, J. Cedervall, A. K. Olsson, C. H. Heldin and J. Lennartsson (2020). "Specific targeting of PDGFRbeta in the stroma inhibits growth and angiogenesis in tumors with high PDGF-BB expression." *Theranostics* 10(3): 1122-1135.

Wang, E. S. (2019). "Incorporating FLT3 inhibitors in the frontline treatment of FLT3 mutant acute myeloid leukemia." *Best Pract Res Clin Haematol* 32(2): 154-162.

The invention claimed is:

1. Crystalline Form I of 1-[2-[5-[(3-Methyl-3-oxetanyl) methoxy]-1H-benzimidazol-1-yl]-8-quinolinyl]-4-piperidinamine monobenzenesulfonate wherein said crystalline form has a powder x-ray diffraction pattern comprising peaks at diffraction angles (2Θ±0.2) 7.1, 14.8, and 18.2.

2. The crystalline form of claim 1, wherein the powder x-ray diffraction pattern has peaks at diffraction angles (2Θ±0.2) 7.1, 14.8, 18.2, 24.3 and 26.9.

3. The crystalline form of claim 1, wherein the powder x-ray diffraction pattern has peaks at diffraction angles (2Θ±0.2) 7.1, 14.8, 16.0, 17.5, 18.2, 24.3, 25.3, and 26.9.

4. The crystalline form of claim 1, wherein the powder x-ray diffraction pattern has peaks at diffraction angles (2Θ±0.2) 7.1, 14.8, 16.0, 16.8, 17.5, 18.2, 19.7, 21.4, 24.3, 25.3, and 26.9.

5. The crystalline form of claim 1, wherein the powder x-ray diffraction pattern has peaks at diffraction angles (2Θ±0.2) 7.1, 8.0, 9.6, 11.4, 11.8, 13.9, 14.5, 14.8, 15.5, 16.0, 16.3, 16.8, 17.5, 18.2, 18.7, 19.3, 19.6, 19.7, 20.0, 20.3, 20.9, 21.4, 21.8, 22.6, 24.3, 25.3, 25.9, 26.9, 28.1, 29.5, 29.9, 31.0, 32.3, 33.4, and 34.3.

6. The crystalline form of claim 1, wherein one or more of (c)-(g) applies:
   (c) said crystalline form has a FT-IR spectrum comprising peaks at about 1479, 1271, 1185, 1033, 824, 751, 728, 690, 612, and 564 cm$^{-1}$;
   (d) said crystalline form is non-hygroscopic;
   (e) said crystalline form has a mass uptake of about 0.9% at 90% RH;
   (f) said crystalline form has birefringent, rod-like morphology; and
   (g) said crystalline form is substantially pure.

7. A pharmaceutical composition comprising the crystalline form of claim 1, and a pharmaceutically acceptable carrier.

8. A method of treating a FLT3 mediated proliferative disorder, comprising administering to a subject in need thereof a therapeutically effective amount of the crystalline form of claim 1, wherein said FLT3 mediated proliferative disorder is selected from the group consisting of Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AM- LITMDS), mixed lineage leukemia (MLL), myelodysplastic syndromes (MDS), myeloproliferative disorders (MPD), multiple myeloma, biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, metastatic esophageal adenocarcinoma, glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, and uterine cancer, or other tumors.

9. A process for the preparation of the crystalline form of claim 1, comprising suspending 1-[2-[5-[(3-Methyl-3-oxetanyl)methoxy]-1H-benzimidazol-1-yl]-8-quinolinyl]-4-piperidinamine monobenzenesulfonate in 1,1-dimethoxymethane or 1-butanol; and then stirring or shaking until precipitation.

10. The method of claim 8, wherein the FLT-3 mediated proliferative disorder is selected from the group consisting of Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AMLITMDS), and mixed lineage leukemia (MLL).

11. The method of claim 8, wherein the FLT-3 mediated proliferative disorder is selected from the group consisting of myelodysplastic syndromes (MDS), myeloproliferative disorders (MPD), multiple myeloma, biliary tract cancer, bladder cancer, breast cancer, cervical cancer, CNS cancer, colon cancer, colorectal carcinoma, esophageal cancer, gastric cancer, gastroesophageal junction (GEJ) adenocarcinoma, gastric adenocarcinoma, stage IIIB gastric adenocarcinoma, stage IV invasive gastric adenocarcinoma, and metastatic esophageal adenocarcinoma.

12. The method of claim 8, wherein the FLT-3 mediated proliferative disorder is selected from the group consisting of glioblastoma, head and neck cancer, hepatocellular carcinoma, liver cancer, lung cancer, melanoma, non-small cell cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, thymoma, and uterine cancer.

13. The method of claim 8, wherein the FLT-3 mediated proliferative disorder is selected from the group consisting of acute myeloid leukemia (AML), breast cancer, colon cancer, colorectal carcinoma, gastric cancer, lung cancer, melanoma, myelodysplastic syndromes (MDS), prostate cancer, and thyroid cancer.

14. The method of claim 8, wherein the FLT-3 mediated proliferative disorder is selected from the group consisting of acute myeloid leukemia (AML), breast cancer, colon cancer, colorectal carcinoma, gastric cancer, lung cancer, and thyroid cancer.

15. The method of claim 8, wherein the FLT-3 mediated proliferative disorder is acute myeloid leukemia (AML).

16. The crystalline form of claim 6, wherein:
(a) said crystalline form has a FT-IR spectrum comprising peaks at about 1479, 1271, 1185, 1033, 824, 751, 728, 690, 612, and 564 cm$^{-1}$;
(b) said crystalline form is non-hygroscopic;
(c) said crystalline form has a mass uptake of about 0.9% at 90% RH;
(d) said crystalline form has birefringent, rod-like morphology; and
(e) said crystalline form is substantially pure.

* * * * *

UNITED STATES PATENT AND TRADEMARK OFFICE
CERTIFICATE OF CORRECTION

PATENT NO. : 11,713,310 B2
APPLICATION NO. : 17/326433
DATED : August 1, 2023
INVENTOR(S) : Vinay Jain It is certified that error appears in the above-identified patent and that said Letters Patent is hereby corrected as shown below:

In the Claims

In Claim 6, at Column 28, Lines 41-51, please cancel the text beginning with "6. The crystalline form" to and ending "is substantially pure." and insert the following claim:
-- 6. The crystalline form of claim 1, wherein one or more of (a) – (e) applies:
    (a) said crystalline form has a FT-IR spectrum comprising peaks at about 1479, 1271, 1185, 1033, 824, 751, 728, 690, 612, and 564 cm-1;
    (b) said crystalline form is non-hygroscopic;
    (c) said crystalline form has a mass uptake of about 0.9% at 90% RH;
    (d) said crystalline form has birefringent, rod-like morphology; and
    (e) said crystalline form is substantially pure. --

In Claim 8, at Column 28, Line 58, the portion of the claim reading "wherein said FLT3 mediated proliferative" should read: -- wherein the FLT3 mediated proliferative --

In Claim 8, at Column 29, Line 16, the portion of the claim reading "uterine cancer, or other tumors." should read: -- uterine cancer. --

Signed and Sealed this
Third Day of September, 2024

Katherine Kelly Vidal
*Director of the United States Patent and Trademark Office*